(12) United States Patent
Sommazzi et al.

(10) Patent No.: US 9,493,404 B2
(45) Date of Patent: Nov. 15, 2016

(54) OXO-NITROGENATED COMPLEX OF COBALT, CATALYTIC SYSTEM COMPRISING SAID OXO-NITROGENATED COMPLEX AND PROCESS FOR THE (CO) POLYMERIZATION OF CONJUGATED DIENES

(71) Applicant: Versalis S.P.A., San Donato Milanese (IT)

(72) Inventors: Anna Sommazzi, Santa Margherita Genova (IT); Giovanni Ricci, Parma (IT); Francesco Masi, Sant' Angelo Lodigiano (IT); Giuseppe Leone, Milan (IT)

(73) Assignee: Versalis S.P.A. (IT)

( * ) Notice: Subject to any disclaimer, the term of this patent is extended or adjusted under 35 U.S.C. 154(b) by 0 days.

(21) Appl. No.: 14/646,051

(22) PCT Filed: Dec. 18, 2013

(86) PCT No.: PCT/IB2013/061078
§ 371 (c)(1),
(2) Date: May 20, 2015

(87) PCT Pub. No.: WO2014/097167
PCT Pub. Date: Jun. 26, 2014

(65) Prior Publication Data
US 2015/0329577 A1   Nov. 19, 2015

(30) Foreign Application Priority Data

Dec. 20, 2012 (IT) .............. MI2012A2201

(51) Int. Cl.
    C08F 4/42       (2006.01)
    C08F 36/06      (2006.01)
    C08F 136/06     (2006.01)
    C07C 251/08     (2006.01)
    C07F 15/06      (2006.01)

(52) U.S. Cl.
    CPC ........... *C07C 251/08* (2013.01); *C07F 15/065* (2013.01); *C08F 36/06* (2013.01); *C08F 136/06* (2013.01)

(58) Field of Classification Search
    CPC .. C08F 4/7008; C08F 4/7095; C08F 4/7096; C08F 36/06; C08F 136/06; C08F 236/06; C07F 15/06; C07F 15/065
    See application file for complete search history.

(56) References Cited

U.S. PATENT DOCUMENTS

| | | |
|---|---|---|
| 3,498,963 A | 3/1970 | Ichikawa et al. |
| 3,522,332 A | 7/1970 | Ichikawa et al. |
| 3,594,216 A * | 7/1971 | Charles et al. ......... C23C 16/18 |
| | | 427/252 |
| 3,966,697 A | 6/1976 | Kampf et al. |
| 4,182,813 A | 1/1980 | Makino et al. |
| 4,285,833 A | 8/1981 | Beck et al. |
| 4,324,939 A | 4/1982 | Hahn et al. |
| 5,128,295 A | 7/1992 | Porri et al. |
| 5,258,475 A | 11/1993 | Kissin |
| 5,548,045 A | 8/1996 | Goto et al. |
| 5,879,805 A | 3/1999 | Brady et al. |
| 5,905,125 A | 5/1999 | Tsujimoto |
| 6,479,601 B1 | 11/2002 | Kerns |
| 7,009,013 B2 | 3/2006 | Shibata et al. |
| 7,868,103 B2 * | 1/2011 | Shiba ..................... C08C 19/10 |
| | | 526/136 |
| 2015/0329651 A1 | 11/2015 | Ricci |

FOREIGN PATENT DOCUMENTS

| | | |
|---|---|---|
| EP | 0277003 A1 | 8/1988 |
| EP | 0418044 A2 | 3/1991 |
| EP | 0421659 A2 | 4/1991 |
| EP | 0427697 A2 | 5/1991 |
| EP | 0495375 A2 | 7/1992 |
| EP | 0520732 A1 | 12/1992 |
| EP | 1367069 A1 | 12/2003 |
| WO | 9200333 A2 | 1/1992 |
| WO | 9205208 A2 | 4/1992 |
| WO | 0110875 | 2/2001 |
| WO | 03/064484 A1 | 8/2003 |
| WO | WO2011061151 | 5/2011 |
| WO | 2011086580 | 7/2011 |

OTHER PUBLICATIONS

Kaabi et al. Transition Metal Chemistry 2007, 32, 666-673.*
Hartl et al. Inorg. Chim. Acta 1986, 118, 57-63.*
Martin et al. J. Am. Chem. Soc. 1961, 83, 73-75.*
Kodama et al. Bull. Chem. Soc. Japan 1972, 45, 1729-1734.*
Gong et al. Polymer 2009, 50, 6259-6264.*
Kim, B. U., in "Studies in Surface Sciences and Catalysis" (2006), vol. 159, pp. 873-876.
Dierkes P. et al., "Journal of Chemical Society, Dalton Transactions" (1999), pp. 1519-1530.
Dudek G. O. and Holm R. H. in "Journal of the American Chemical Society" (1961), vol. 83, Issue 9, pp. 2099-2104.
Endo K. et al., "Journal of Polymer Science: Part A: Polymer Chemistry" (2006), vol. 44, pp. 4088-4094.

(Continued)

*Primary Examiner* — Rip A Lee
(74) *Attorney, Agent, or Firm* — Abel Law Group, LLP

(57) ABSTRACT

The present invention relates to an oxo-nitrogenated complex of cobalt having the general formula (I) wherein the residues $R_1$, $R_2$, $R_3$, $X_1$ and $X_2$ are as defined in the claims. Said oxo-nitrogenated complex of cobalt having general formula (I) can be advantageously used in a catalytic system for the (co) polymerization of conjugated dienes.

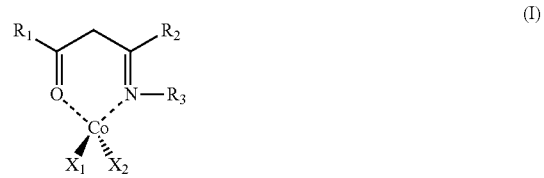

(I)

13 Claims, 10 Drawing Sheets

(56) References Cited

OTHER PUBLICATIONS

Freixa Z. et al, "Dalton Transactions" (2003), pp. 1890-1901.
Furukawa J. et al., "Polymer Journal" (1971), vol. 2, pp. 371-378.
Gong D. et al., "Polymer" (2009), vol. 50, pp. 6259-6264.
Gong D. et al "Journal of Organometallic Chemistry" (2011), vol. 696, pp. 1584-1590.
Bianchini, C., in "European Journal of Inorganic Chemistry" (2003), pp. 1620-1631.
Ai, Pengfei, et al. "Polymerization of 1, 3-butadiene catalyzed by cobalt (II) and nickel (II) complexes bearing imino-or aminopyridyl alcohol ligands in combination with ethylaluminum sesquichloride." Journal of Organometallic Chemistry 705 (2012): 51-58.
Johnson et al. "Journal of the American Chemical Society" (1995), vol. 117, pp. 6414-6415.
Kaabi, Ilhem, et al. "Crystal structure of a new pentadentate symmetrical: di [4-(phenylimino) pentan-2-one] ether. Structural and electrochemical studies of its Coll, Nill, Cull and Cdll complexes." Transition Metal Chemistry 32.5 (2007): 666-673.
Nobbs, J. D., in "The Royal Society of Chemistry" (2012), vol. 41, pp. 5949-5964.
Osakada, K. et al., "Advances in Polymer Science" (2004), vol. 171, pp. 137-194.
Ricci G. et al., "Cobalt: Characteristics, Compounds, and Applications" (2011), Lucas J. Vidmar Ed., Nova Science Publisher, Inc., USA, pp. 39-81.
Ricci G. et al., "Journal of Organometallic Chemistry" (2005), vol. 690, pp. 1845-1854.
Ricci G. et al., "Journal of Molecular Catalysis A: Chemical" (2005), vol. 226, pp. 235-241.
Ricci G. et al., "Polymer Communications" (1991), vol. 32, pp. 514-517.
Ricci G. et al., "Polymer Communications" (1988), vol. 29, pp. 305-307.
Strauss, S. H. "Chemical Reviews" (1993), vol. 93, pp. 927-942.
Takeuchi Y. et al., "New Industrial Polymers", "American Chemical Society Symposium Series" (1974), vol. 4, pp. 15-25.
Takeuchi M. et al., "Polymer International" (1992), vol. 29, pp. 209-212.
Takeuchi M. et al., "Polymer International" (1995), vol. 36, pp. 41-45.
Takeuchi M. et al., "Macromolecular Chemistry and Physics" (1996), vol. 197, pp. 729-743.
Chandran, Deepak, et al. "Polymerization of 1, 3-butadiene by bis (salicylaldiminate) cobalt (II) catalysts combined with organoaluminium cocatalysts." Catalysis Today 131.1 (2007): 505-512.
Thiele S. K. H. et al., "Journal of Macromolecular Science. Part C: Polymer Reviews" (2003), C43, pp. 581-628.
Tolman C., "Chemical Reviews" (1977), vol. 77, pp. 313-348.
van Koten et al. in "Advances in Organometallic Chemistry" (1982), vol. 21, pp. 151-239.
van Leeuwen P. et al., "Chemical Reviews" (2000), vol. 100, pp. 2741-2769.
Hartl, F., and A. Vlček. "Oxidative addition of quinones to planar cobalt (II) dithiolato, dithioacetylacetonato and Schiff-base complexes." Inorganica chimica acta 118.1 (1986): 57-63.
Martin, Dean F. "Journal of the American Chemical Society," vol. 83, No. 1, Jan. 5, 1961, p. 73-75.
Jie, Suyun, Pengfei Ai, and Bo-Geng Li. "Highly active and stereospecific polymerization of 1, 3-butadiene catalyzed by dinuclear cobalt (ii) complexes bearing 3-aryliminomethyl-2-hydroxybenzaldehydes." Dalton Transactions 40.41 (2011): 10975-10982.
International Search Report dated Apr. 1, 2014 for PCT/IB2013/061078.
Appukuttan et al., in "Polymer" (2009), vol. 50, pp. 1150-1158.
Appukuttan, Vinukrishnan, et al. "Stereospecific polymerizations of 1, 3-butadiene catalyzed by Co (II) complexes ligated by 2, 6-bis (benzimidazolyl) pyridines." Journal of Molecular Catalysis A: Chemical 325.1 (2010): 84-90.
Ashitaka H. et al., "Journal of Polymer Science: Polymer Chemistry Edition" (1983), vol. 21, pp. 1853-1860.
Ashitaka H. et al., "Journal of Polymer Science: Polymer Chemistry Edition" (1983), vol. 21, pp. 1951-1972.
Ashitaka H. et al., "Journal of Polymer Science: Polymer Chemistry Edition" (1983), vol. 21, pp. 1973-1988.
Ashitaka H. et al., "Journal of Polymer Science: Polymer Chemistry Edition" (1983), vol. 21, pp. 1989-1995.
Beck et al., "Chemical Reviews" (1988), vol. 88, pp. 1405-1421.
Cariou R. et al., "Dalton Transactions" (2010), vol. 39, pp. 9039-9045.
Kerns M. et al., "Butadiene Polymers", in "Encyclopedia of Polymer Science and Technology" (2003), Mark H. F. Ed., Wiley, vol. 5, pp. 317-356.
Kim J. S. et al., "e-Polymer" (European Polymer Federation) (2006), No. 27.
Natta G. et al., "Chemical Communications" (1967), Issue 24, pp. 1263-1265.
Osakada, K. et al., "Advanced Polymer Science" (2004), vol. 171, pp. 137-194.
Parks J. E. and Holm R. H. in "Inorganic Chemistry" (1968), vol. 7(7), pp. 1408-1416.
Porri L. et al., "Comprehensive Polymer Science" (1989), Eastmond G.C. et al. Eds., Pergamon Press, Oxford, UK, vol. 4, Part II, pp. 53-108.
Racanelli P. et al., "European Polymer Journal" (1970), vol. 6, pp. 751-761.
Roberts E. and Turner E. E. in "Journal of Chemical Society" (1927), pp. 1832-1857.
Ricci G. et al., "Advances in Organometallic Chemistry Research" (2007), Yamamoto K. Ed., Nova Science Publisher, Inc., USA, pp. 1-36.
Ricci G. et al., "Coordination Chemistry Reviews" (2010), vol. 254, pp. 661-676.
Ricci G. et al., "Macromolecules" (2005), vol. 38, pp. 1064-1070.

* cited by examiner

FT-IR spectrum of the $CoCl_2(L4)$ complex [sample GL924] (Example 5)

(the nujol bands have been subtracted)

FT-IR spectrum of the $CoCl_2(L6)$complex [sample GL927] (Example 6)

(the nujol bands have been subtracted)

$^{13}$C-NMR spectrum (on the left) and $^1$H-NMR spectrum (on the right)

of the polybutadiene of Example 7

(A)

(B)

DSC diagrams of the polybutadiene of Example 9: (A) crystallization; (B) melting $^{13}$C-NMR spectrum (on the left) and $^{1}$H-NMR spectrum (on the right)

of the polybutadiene of Example 9

(A)

(B)

DSC diagrams of the polybutadiene of Example 10: (A) crystallization; (B) melting $^{13}$C-NMR spectrum (on the left) and $^1$H-NMR spectrum (on the right)

of the polybutadiene of Example 10

FT-IR spectrum of the polybutadiene of Example 11 (GL979)

(A)

(B)

DSC diagrams of the polybutadiene of Example 11: (A) crystallization; (B) melting (A)

(B)

DSC diagrams of the polybutadiene of Example 12: (A) crystallization; (B) melting

OXO-NITROGENATED COMPLEX OF COBALT, CATALYTIC SYSTEM COMPRISING SAID OXO-NITROGENATED COMPLEX AND PROCESS FOR THE (CO) POLYMERIZATION OF CONJUGATED DIENES

The present invention relates to an oxo-nitrogenated complex of cobalt.

More specifically, the present invention relates to an oxo-nitrogenated complex of cobalt and to its use in a catalytic system for the (co)polymerization of conjugated dienes.

The present invention also relates to a catalytic system for the (co)polymerization of conjugated dienes comprising said oxo-nitrogenated complex of cobalt.

Furthermore, the present invention relates to a process for the (co)polymerization of conjugated dienes, in particular to a process for the (co)polymerization of 1,3-butadiene or isoprene, characterized in that it uses said catalytic system.

It is known that the stereospecific (co)polymerization of conjugated dienes is an extremely important process in the chemical industry for obtaining products which are among the most widely-used rubbers.

It is also known that among the various polymers that can be obtained from the stereospecific polymerization of 1,3-butadiene (i.e. 1,4-cis, 1,4-trans, 1,2 syndiotactic, 1,2 isotactic, 1,2 atactic, mixed 1,4-cis/1,2 structure having a variable content of 1,2 units), only 1,4-cis polybutadiene and syndiotactic 1,2 polybutadiene are produced industrially and commercialized. Further details relating to these polymers can be found, for example, in: Takeuchi Y. et al., "*New Industrial Polymers*", "*American Chemical Society Symposium Series*" (1974), Vol. 4, pages 15-25; Halasa A. F. et al., "*Kirk-Othmer Encyclopedia of Chemical Technology*" (1989), 4$^{th}$ Ed., Kroschwitz J. I. Ed., John Wiley and Sons, New York, Vol. 8, pages 1031-1045; Tate D. et al., "*Encyclopedia of Polymer Science and Engineering* (1989), 2$^{nd}$ Ed., Mark H. F. Ed., John Wiley and Sons, New York, Vol. 2, pages 537-590; Kerns M. et al., "*Butadiene Polymers*", in "*Encyclopedia of Polymer Science and Technology*" (2003), Mark H. F. Ed., Wiley, Vol. 5, pages 317-356.

1,4-cis polybutadiene is a synthetic elastomer, generally having a content of 1,4-cis units equal to 96%-97%, a melting point ($T_m$) of about −2° C., a crystallization temperature ($T_c$) of about −25° C. and a glass transition temperature ($T_g$) below −100° C., whose properties are very similar to those of natural rubber and whose main use is in the production of tyres for motor vehicles and/or trucks. In particular, in the production of tyres, polybutadiene with a high content of 1,4-cis units is used.

1,4-cis polybutadiene is generally prepared through polymerization processes which use various catalytic systems comprising catalysts based on titanium (Ti), cobalt (Co), nickel (Ni), neodymium (Nd). Catalytic systems comprising catalysts based on cobalt have a high catalytic activity and stereospecificity and can be considered as being the most versatile among those listed above as, by varying their formulation, they are capable of providing all the possible stereoisomers of polybutadiene indicated above, as described, for example, in: Porri L. et al., "*Comprehensive Polymer Science*" (1989), Eastmond G. C. et al. Eds., Pergamon Press, Oxford, UK, Vol. 4, Part II, pages 53-108; Thiele S. K. H. et al., "*Macromolecular Science. Part C: Polymer Reviews*" (2003), C43, pages 581-628; Osakada, K. et al., "*Advanced Polymer Science*" (2004), Vol. 171, pages 137-194; Ricci G. et al., "*Advances in Organometallic Chemistry Research*" (2007), Yamamoto K. Ed., Nova Science Publisher, Inc., USA, pages 1-36; Ricci G. et al., "*Coordination Chemistry Reviews*" (2010), Vol. 254, pages 661-676; Ricci G. et al., "*Cobalt: Characteristics, Compounds, and Applications*" (2011), Lucas J. Vidmar Ed., Nova Science Publisher, Inc., USA, pages 39-81.

The catalytic system cobalt bis-acetylacetonate/di-ethyl-aluminium chloride/water [Co(acac)$_2$/AlEt$_2$Cl/H$_2$O], for example, provides a polybutadiene having a content of 1,4-cis units equal to about 97% and it is that normally used for the industrial production of this polymer as described, for example, in Racanelli P. et al., "*European Polymer Journal*" (1970), Vol. 6, pages 751-761. The catalytic system cobalt tris-acetylacetonate/methylaluminoxane [Co(acac)$_3$/MAO] also provides a polybutadiene having a content of 1,4-cis units equal to about 97%, as described, for example in: Ricci G. et al., "*Polymer Communication*" (1991), Vol. 32, pages 514-517.

The catalytic system cobalt tris-acetylacetonate/tri-ethyl-aluminium/water[Co(acac)$_3$/AlEt$_3$/H$_2$O], on the other hand, provides a polybutadiene having a mixed 1,4-cis/1,2 equibinary structure as described, for example, in: Furukawa J. et al., "*Polymer Journal*" (1971), Vol. 2, pages 371-378. Said catalytic system, in the presence of carbon disulfide (CS$_2$), is used, on the other hand, in processes for the industrial production of highly crystalline 1,2 syndiotactic polybutadiene: further details relating to these processes can be found, for example, in: Ashitaka H. et al., "*Journal of Polymer Science: Polymer Chemistry Edition*" (1983), Vol. 21, pages 1853-1860; Ashitaka H. et al., "*Journal of Polymer Science: Polymer Chemistry Edition*" (1983), Vol. 21, pages 1951-1972; Ashitaka H. et al., "*Journal of Polymer Science: Polymer Chemistry Edition*" (1983), Vol. 21, pages 1973-1988; Ashitaka H. et al., "*Journal of Polymer Science: Polymer Chemistry Edition*" (1983), Vol. 21, pages 1989-1995.

An extremely active and stereospecific catalytic system for the preparation of 1,2-syndiotactic polybutadiene can be obtained by the combination of the allyl complex of cobalt ($\eta^4$-C$_4$H$_6$)($\eta^5$-C$_8$H$_{13}$)Co described, for example, by Natta G. et al., "*Chemical Communications*" (1967), Issue 24, pages 1263-1265, with carbon disulfide (CS$_2$), as described, for example, in: Ricci G. et al., "*Polymer Communication*" (1988), Vol. 29, pages 305-307. Said catalytic system is capable of dimerizing 1,3-butadiene at room temperature, as described, for example, in U.S. Pat. No. 5,879,805, but is only capable of giving 1,2-syndiotactic polymers when operating at low temperatures (−30° C.) as described, for example, in: Ricci G. et al., "*Polymer Communication*" (1988), Vol. 29, pages 305-307.

1,2-syndiotactic polybutadienes can also be produced using catalytic systems obtained by a combination of cobalt dichloride (CoCl$_2$) or cobalt dibromide (CoBr$_2$) with organic compounds of aluminium (e.g., alkyl compounds of aluminium), water and phosphines (e.g., triphenylphosphine) as described, for example in the following American patents: U.S. Pat. No. 5,879,805, U.S. Pat. No. 4,324,939, U.S. Pat. No. 3,966,697, U.S. Pat. No. 4,285,833, U.S. Pat. No. 3,498,963, U.S. Pat. No. 3,522,332, U.S. Pat. No. 4,182,813, U.S. Pat. No. 5,548,045, U.S. Pat. No. 7,009,013. The regioregularity and crystallinity of the polybutadienes obtained with said catalytic systems are much lower (e.g., 80%-90% of 1,2 units, melting point ($T_m$) ranging from 75° C. to 90° C.) with respect to those of the polybutadienes obtained with the catalytic system described in: Ricci G. et al., "*Polymer Communication*" (1988), Vol. 29, pages 305-307, indicated above.

Further details relating to the polymerization of 1,3-butadiene with catalytic systems comprising complexes of cobalt with various phosphines are provided, for example, in: Ricci G. et al., "*Macromolecules*" (2005), Vol. 38, pages 1064-1070; Ricci G. et al., "*Journal of Organometallic Chemistry*" (2005), Vol. 690, pages 1845-1854; Takeuchi M. et al., "*Polymer International*" (1992), Vol. 29, pages 209-212; Takeuchi M. et al., "*Polymer International*" (1995), Vol. 36, pages 41-45; Takeuchi M. et al., "*Macromolecular Chemistry and Physics*" (1996), Vol. 197, pages 729-743; or in Italian patents IT 1,349,141, IT 1,349,142, IT 1,349,143. The use of different phosphines derives from the fact that it is well known how the steric and electronic properties of phosphines greatly depend on the type of substituents on the phosphorous atom as described, for example, in: Dierkes P. et al., "*Journal of Chemical Society, Dalton Transactions*" (1999), pages 1519-1530; van Leeuwen P. et al., "*Chemical Reviews*" (2000), Vol. 100, pages 2741-2769; Freixa Z. et al, "*Dalton Transactions*" (2003), pages 1890-1901; Tolman C., "*Chemical Reviews*" (1977), Vol. 77, pages 313-348.

The documents relating to the use of phosphines indicated above, show how the use of phosphine complexes of cobalt combined with methylaluminoxane (MAO) can allow the microstructure of polybutadiene to be managed, thus allowing polybutadienes with different structures to be obtained, depending on the type of phosphine coordinated with the cobalt atom.

The polymerization of 1,3-butadiene with catalytic systems comprising complexes of cobalt with sterically hindered aliphatic phosphines (e.g., P$^t$Bu$_3$, P$^i$Pr$_3$, P$^t$Bu$_2$Me, PCy$_3$, PCyp$_3$ wherein P=phosphorous, $^t$Bu=tert-butyl, $^i$Pr=iso-propyl, Cy=cyclohexyl and Cyp=cyclopentyl), provides polybutadienes with a prevalently 1,4-cis structure, whereas polybutadienes having a mixed 1,4-cis/1,2 structure have been obtained using catalytic systems comprising complexes of cobalt with phosphines having a lower steric hindrance (e.g., PCy$_2$H; P$^t$Bu$_2$H; PEt$_3$; P$^n$Pr$_3$ wherein P=phosphorous, Cy=cyclohexyl, $^t$Bu=tert-butyl, Et=ethyl and $^n$Pr=n-propyl), as described, for example, in: Ricci G. et al., "*Advances in Organometallic Chemistry Research*" (2007), Yamamoto K. Ed., Nova Science Publisher, Inc., USA, pages 1-36; Ricci G. et al., "*Coordination Chemistry Reviews*" (2010), Vol. 254, pages 661-676; Ricci G. et al., "*Journal of Molecular Catalysis A: Chemical*" (2005), Vol. 226, pages 235-241; and in Italian patent application IT 1,349,141.

Polybutadienes with a high content of 1,4-cis units (about 95%) have been obtained with catalytic systems comprising complexes of cobalt with bidentate phosphines [e.g., CoCl$_2$[R$_2$P(CH$_2$)$_n$PR$_2$]/MAO, wherein Co=cobalt, Cl=chlorine, R=methyl, ethyl, phenyl, n=1 or 2, P=phosphorous and MAO=methylaluminoxane), regardless of the type of bidentate phosphine coordinated with the cobalt atom, as described, for example, in: Ricci G. et al., "*Advances in Organometallic Chemistry Research*" (2007), Yamamoto K. Ed., Nova Science Publisher, Inc., USA, pages 1-36; Ricci G. et al., "*Coordination Chemistry Reviews*" (2010), Vol. 254, pages 661-676; and in Italian patent application IT 1,349,141.

Catalytic systems comprising complexes of cobalt with ligands selected from aromatic phosphines [e.g., CoCl$_2$(PRPh$_2$)$_2$/MAO (wherein Co=cobalt, Cl=chlorine, P=phosphorous, R=methyl, n-propyl, ethyl, iso-propyl, cyclohexyl, Ph=phenyl, MAO=methylaluminoxane] have, on the other hand, proved to be extremely active for the 1,2 polymerization of 1,3-butadiene as described, for example, in: Ricci G. et al., "*Advances in Organometallic Chemistry Research*" (2007), Yamamoto K. Ed., Nova Science Publisher, Inc., USA, pages 1-36; Ricci G. et al., "*Coordination Chemistry Reviews*" (2010), Vol. 254, pages 661-676; Ricci G. et al., "*Macromolecules*" (2005), Vol. 38, pages 1064-1070; Ricci G. et al., "*Journal of Organometallic Chemistry*" (2005), Vol. 690, pages 1845-1854; or in Italian patent application IT 1,349,143. Using these catalytic systems, in fact, polybutadienes with an essentially 1,2 structure have been obtained (within a range of 70% to 88%), having a variable content of 1,2 units in relation to the type of complex and of polymerization conditions. It has also been observed that the tacticity of the polybutadienes obtained greatly depends on the type of complex, i.e. the type of phosphine bound to the cobalt atom and that the syndiotacticity index (expressed as a percentage of syndiotactic triads "rr"), determined by the $^{13}$C-NMR spectra, increases with an increase in the steric requirement of the alkyl group bound to the phosphorous atom.

The 1,2 polybutadienes obtained with less sterically hindered cobalt systems with phosphine ligands (e.g., PMePh$_2$; PEtPh$_2$; P$^n$PrPh$_2$ wherein P=phosphorous, Me=methyl, Ph=phenyl, $^n$Pr=n-propyl) have proved to be amorphous, whereas the polybutadienes obtained with catalytic systems using phosphine ligands with a higher steric hindrance (e.g., P$^i$PrPh$_2$, PCyPh$_2$ wherein P=phosphorous, $^i$Pr=iso-propyl, Ph=phenyl, Cy=cyclohexyl), have proved to be crystalline, with a melting point (T$_m$) of 110° C.-120° C., depending on the polymerization conditions.

The polymerization of 1,3-butadiene with catalytic systems comprising complexes of cobalt with aromatic phosphines having the formula CoCl$_2$(PR$_2$Ph)$_2$/MAO (wherein Co=cobalt, Cl=chlorine, R=methyl, ethyl, cyclohexyl, Ph=phenyl, MAO=methylaluminoxane), has also been studied, as described, for example, in: Ricci G. et al., "*Advances in Organometallic Chemistry Research*" (2007), Yamamoto K. Ed., Nova Science Publisher, Inc., USA, pages 1-36; Ricci G. et al., "*Coordination Chemistry Reviews*" (2010), Vol. 254, pages 661-676; Ricci G. et al., "*Journal of Organometallic Chemistry*" (2005), Vol. 690, pages 1845-1854; or in Italian patent application IT 1,349,143. Using said catalytic systems, essentially 1,2-polybutadienes have been obtained, but the syndiotacticity index of the polymers, with the same polymerization conditions, has generally proved to be slightly lower with respect to that of the 1,2-polybutadienes obtained with catalytic systems comprising complexes of cobalt with aromatic phosphines having the formula CoCl$_2$(PRPh)$_2$/MAO described above.

More recently, following the success obtained using the above catalytic systems comprising phosphine complexes of cobalt, different catalytic systems comprising complexes of cobalt with ligands containing nitrogen or oxygen as donor atom, have been studied.

Kim J. S. et al., in "*e-Polymer*" (*European Polymer Federation*) (2006), No. 27, for example, describe the polymerization of 1,3-butadiene with catalytic systems comprising complexes of cobalt with bis(imine)pyridine and ethylaluminiumsesquichloride [Al$_2$Et$_3$Cl$_3$ (EASC)] ligands. Said catalytic systems have proved to be particularly active, providing high-molecular-weight polybutadienes having a content of 1,4-cis units equal to 96.4%.

Catalytic systems comprising complexes of cobalt having the formula (Salen)Co(II) (wherein Salen=bis(salicylaldehyde)ethylenediiminate, Co=cobalt) and methylaluminoxane (MAO), characterized by a high activity and 1,4-cis selectivity, are described, for example by Endo K. et al., in "*Journal of Polymer Science: Part A: Polymer Chemistry*" (2006), vol. 44, pages 4088-4094.

Cariou R. et al., in "*Dalton Transactions*" (2010), Vol. 39, pages 9039-9045, describe the synthesis and the characterization of a series of complexes of cobalt (II) [Co(II)] with bis(benzimidazole) which, when combined with methylaluminoxane (MAO), have proved to be highly selective for the 1,4-cis polymerization of 1,3-butadiene.

The synthesis and the characterization of a series of complexes of cobalt (II) [Co(II)] with dibenzimidazole ligands and their use, combined with ethylaluminiumsesquichloride (EASC), for the polymerization of 1,3-butadiene, are described by Appukuttan et al., in "*Polymer*" (2009), Vol. 50, pages 1150-1158: the catalytic systems obtained are characterized by a high catalytic activity and also a high 1,4-cis selectivity (up to 97%).

Complexes of cobalt with 2,6-bis[1-(iminophenyl)ethyl] pyridine ligands were synthesized and characterized by Gong D. et al., as described in "*Polymer*" (2009), Vol. 50, pages 6259-6264. Said complexes, combined with methylaluminoxane (MAO), were tested for the polymerization of 1,3-butadiene, providing catalytic systems capable of giving 1,4-cis or 1,4-trans polybutadiene, in relation to the MAO/Co ratio. When operating with a MAO/Co molar ratio equal to 50, in fact, an essentially 1,4 trans polybutadiene was obtained (about 94.4%), whereas, when operating with a MAO/Co molar ratio equal to 100, a prevalently 1,4-cis polybutadiene was obtained (about 79%).

In "*Journal of Molecular Catalysis A: Chemical*" (2010), Vol. 325, pages 84-90, Appukuttan V. et al., describe a series of complexes having general formula [Py(Bm-R)$_2$]CoCl$_2$ (wherein Py=pyridyl, Bm=benzimidazolyl, R=hydrogen, methyl, benzimidazole, Co=cobalt, Cl=chlorine), capable of providing, when combined with methylaluminoxane (MAO), high-molecular-weight 1,4-cis polybutadiene.

In "*Journal of Organometallic Chemistry*" (2011), Vol. 696, pages 1584-1590, Gong D. et al., describe a series of 2,6-bis(imino)pyridine complexes of cobalt (II) [Co(II)] which, when combined with methylaluminoxane (MAO) as co-catalyst, show a relatively good activity in the polymerization of 1,3-butadiene, allowing a polybutadiene to be obtained, having a 1,4-cis microstructure within a range of 77.5% to 97%, with control of both the molecular weight and also the molecular weight distribution.

Finally, Jie S. et al., in "*Dalton Transactions*" (2011), Vol. 40, pages 10975-10982 and Ai P. et al., in "*Journal of Organometallic Chemistry*" (2012), Vol. 705, pages 51-58, have recently described the possibility of obtaining polybutadiene with a high content of 1,4-cis units (>96%) with catalytic systems comprising catalysts based on complexes of cobalt with 3-aryliminomethyl-2-hydroxybenzaldehyde ligands, or with ligands of the NNO type (imino- or amino-pyridyl alcohols), respectively.

As already indicated above, as (co)polymers of conjugated dienes, in particular polybutadiene and polyisoprene with a high content of 1,4-cis units, are the most widely-used polymers on an industrial scale, in particular for the production of tyres, the study of new catalytic systems capable of providing these (co)polymers is still of great interest.

Figure 1:
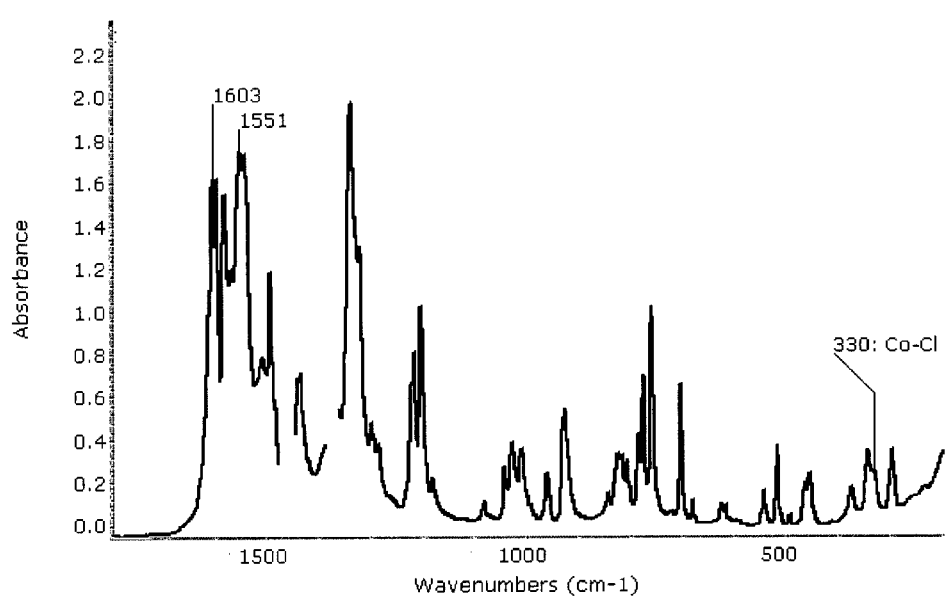
FIG. 1: FT-IR spectrum of the CoCl2(L4) complex [sample GL924] (Example 5) (the nujol bands have been subtracted)

The Applicant has considered the problem of finding a new complex of cobalt which can be used in a catalytic system capable of giving (co)polymers of conjugated dienes, such as, for example, polybutadiene, polyisoprene, in particular linear or branched polybutadiene, with a high content of 1,4-cis units, i.e. a content of 1,4-cis units ≥96%.

The Applicant has now found a new oxo-nitrogenated complex of cobalt having general formula (I) defined hereunder, capable of giving (co)polymers of conjugated dienes, such as, for example, polybutadiene, polyisoprene, in particular linear or branched polybutadiene, with a high content of 1,4-cis units, i.e. a content of 1,4-cis units ≥96%.

An object of the present invention therefore relates to an oxo-nitrogenated complex of cobalt having general formula (I):

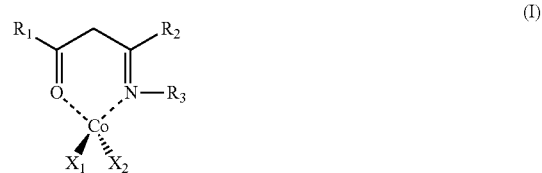

wherein:
R$_1$ and R$_2$, equal to or different from each other, represent a hydrogen atom, or they are selected from linear or branched C$_1$-C$_{20}$, preferably C$_1$-C$_{15}$, alkyl groups, optionally halogenated, cycloalkyl groups optionally substituted, aryl groups optionally substituted;

R$_3$ represents a hydrogen atom, or it is selected from linear or branched C$_1$-C$_{20}$, preferably C$_1$-C$_{15}$, alkyl groups optionally halogenated, cycloalkyl groups optionally substituted, aryl groups optionally substituted; or R$_3$ represents a ketoimine group having formula:

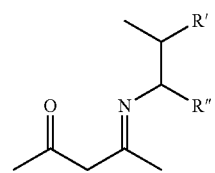

wherein R' and R", equal to or different from each other, represent a hydrogen atom, or they are selected from linear or branched C$_1$-C$_{20}$, preferably C$_1$-C$_{15}$, alkyl groups, cycloalkyl groups optionally substituted, aryl groups optionally substituted;

$X_1$ and $X_2$, equal to or different from each other, represent a halogen atom such as, for example, chlorine, bromine, iodine; or they are selected from linear or branched $C_1$-$C_{20}$, preferably $C_1$-$C_{15}$, alkyl groups, —$OCOR_4$ groups or —$OR_4$ groups wherein $R_4$ is selected from linear or branched $C_1$-$C_{20}$, preferably $C_1$-$C_{15}$, alkyl groups.

For the aim of the present description and of the following claims, the definitions of the numerical intervals always include the extremes, unless otherwise specified.

For the aim of the present description and of the following claims, the term "comprising" also includes the terms "which essentially consist of" or "which consists of".

The term "$C_1$-$C_{20}$ alkyl groups" refers to linear or branched alkyl groups having from 1 to 20 carbon atoms. Specific examples of $C_1$-$C_{20}$ alkyl groups are: methyl, ethyl, n-propyl, iso-propyl, n-butyl, s-butyl, iso-butyl, tert-butyl, pentyl, hexyl, heptyl, octyl, n-nonyl, n-decyl, 2-butyloctyl, 5-methylhexyl, 4-ethylhexyl, 2-ethylheptyl, 2-ethylhexyl.

The term "$C_1$-$C_{20}$ alkyl groups optionally halogenated" refers to linear or branched alkyl groups having from 1 to 20 carbon atoms, saturated or unsaturated, wherein at least one of the hydrogen atoms is substituted with a halogen atom such as, for example, fluorine, chlorine, bromine, preferably fluorine, chlorine. Specific examples of $C_1$-$C_{20}$ alkyl groups optionally halogenated are: fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl, perfluoropentyl, perfluoroctyl, perfluorodecyl.

The term "cycloalkyl groups" refers to cycloalkyl groups having from 3 to 30 carbon atoms. Said cycloalkyl groups can be optionally substituted with one or more groups, equal to or different from each other, selected from: halogen atoms; hydroxyl groups; $C_1$-$C_{12}$ alkyl groups; $C_1$-$C_{12}$ alkoxyl groups; cyano groups; amino groups; nitro groups. Specific examples of cycloalkyl groups are: cyclopropyl, 2,2-difluorocyclopropyl, cyclobutyl, cyclopentyl, cyclohexyl, hexamethylcyclohexyl, pentamethyl-cyclopentyl, 2-cyclooctylethyl, methylcyclohexyl, methoxycyclohexyl, fluorocyclohexyl, phenylcyclohexyl.

The term "aryl groups" refers to aromatic carbocyclic groups. Said aromatic carbocyclic groups can be optionally substituted with one or more groups, equal to or different from each other, selected from: halogen atoms such as, for example, fluorine, chlorine, bromine; hydroxyl groups; $C_1$-$C_{12}$ alkyl groups; $C_1$-$C_{12}$ alkoxyl groups, cyano groups; amino groups; nitro groups. Specific examples of aryl groups are: phenyl, methylphenyl, trimethylphenyl, methoxyphenyl, hydroxyphenyl, phenyloxyphenyl, fluorophenyl, pentafluorophenyl, chlorophenyl, bromophenyl, nitrophenyl, dimethylaminophenyl, naphthyl, phenylnaphthyl, phenanthrene, anthracene.

According to a preferred embodiment of the present invention, in said oxo-nitrogenated complex of cobalt having general formula (I):

$R_1$ and $R_2$, the same as each other, are a hydrogen atom; or they are selected from linear or branched $C_1$-$C_{20}$ alkyl groups, preferably are a methyl group;

$R_3$ is selected from linear or branched $C_1$-$C_{20}$ alkyl groups, or phenyl groups optionally substituted with linear or branched $C_1$-$C_{20}$ alkyl groups, preferably substituted with one or more methyl, ethyl, iso-propyl groups; or $R_3$ represents a ketoimine group having formula:

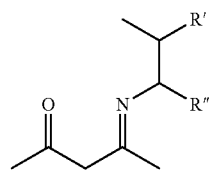

wherein R' and R", the same as each other, represent a hydrogen atom;

$X_1$ and $X_2$, the same as each other, are a halogen atom such as, for example, chlorine, bromine, iodine, preferably chlorine.

The oxo-nitrogenated complex of cobalt having general formula (I), should be considered, according to the present invention, as being in any physical form such as, for example, in the form of an isolated and purified solid, solvated with a suitable solvent, or supported on suitable organic or inorganic solids, preferably having a granular or powder physical form.

The oxo-nitrogenated complex of cobalt having general formula (I) is prepared starting from ligands known in the art.

Specific examples of ligands which can be used for the aim of the present invention are those having the following formulae (L1)-(L6):

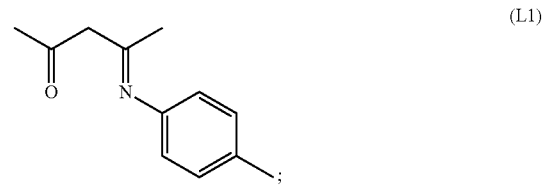

(L1)

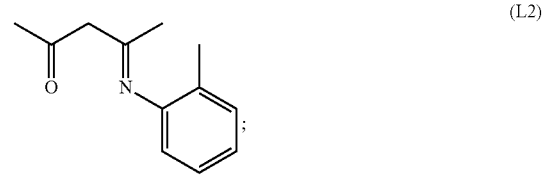

(L2)

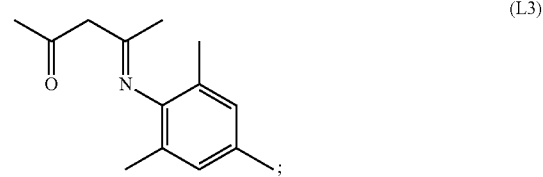

(L3)

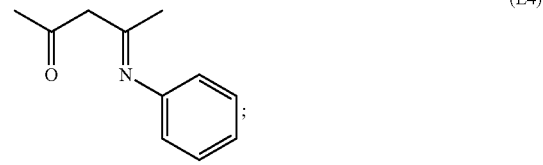

(L4)

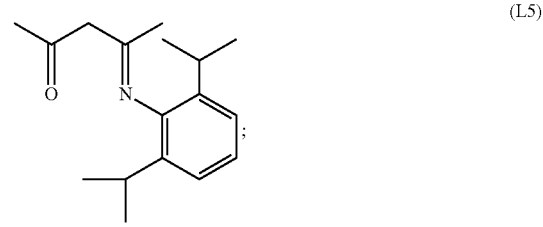

(L5)

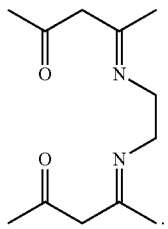 (L6)

Said ligands having formulae (L1)-(L6) can be prepared by means of processes known in the art. Said ligands having formulae (L1)-(L6) can be prepared, for example, by means of condensation reactions between primary amines and diketones, as described, for example, in international patent application WO 2001/10875; or by: Parks J. E. and Holm R. H. in "*Inorganic Chemistry*" (1968), Vol 7(7), pages 1408-1416; Roberts E. and Turner E. E. in "*Journal of Chemical Society*" (1927), pages 1832-1857; Dudek G. O. and Holm R. H. in "*Journal of the American Chemical Society*" (1961), Vol. 83, Issue 9, pages 2099-2104.

The oxo-nitrogenated complex of cobalt having general formula (I) can be prepared by means of processes known in the art. Said oxo-nitrogenated complex of cobalt can be prepared, for example, by the reaction between cobalt compounds having general formula Co(X)$_2$ wherein X is a halogen atom such as, for example, chlorine, bromine, iodine, preferably chlorine, as such or complexed with ethers [for example, diethylether, tetrahydrofuran (THF), dimethoxyethane], with the ligands having formulae (L1)-(L6) indicated above, in a ligand (L)/cobalt (Co) molar ratio ranging from 1 to 1.5, preferably operating in the presence of at least one solvent which can be selected, for example, from: chlorinated solvents (for example, methylene chloride), ether solvents [for example, tetrahydrofuran (THF)], alcohol solvents (for example, butanol), hydrocarbon solvents (for example, toluene), or mixtures thereof, at room temperature or higher. The oxo-nitrogenated complex of cobalt thus obtained can be subsequently recovered by means of methods known in the art such as, for example, precipitation by means of a non-solvent (for example, pentane), followed by separation by means of filtration or decanting and optional subsequent dissolution in a suitable solvent followed by crystallization at a low temperature.

For the aim of the present description and of the following claims, the phrase "room temperature" refers to a temperature ranging from 20° C. to 25° C.

As already specified above, the present invention also relates to a catalytic system for the (co)polymerization of conjugated dienes comprising said oxo-nitrogenated complex of cobalt having general formula (I).

A further object of the present invention therefore relates to a catalytic system for the (co)polymerization of conjugated dienes comprising.

(a) at least one oxo-nitrogenated complex of cobalt having general formula (I);
(b) at least one co-catalyst selected from organic compounds of an element M' different from carbon, said element M' being selected from elements belonging to groups 2, 12, 13 or 14, of the Periodic Table of Elements, preferably from: boron, aluminium, zinc, magnesium, gallium, tin, even more preferably aluminium, boron.

The formation of the catalytic system comprising the oxo-nitrogenated complex of cobalt having general formula (I) and the co-catalyst (b) is generally and preferably carried out in an inert liquid medium, more preferably in a hydrocarbon solvent. The choice of the oxo-nitrogenated complex of cobalt having general formula (I) and of the co-catalyst (b), as well as the particular method used, can vary in relation to the molecular structures and to the desired result, according to what is analogously described in specific literature available to experts in the field for other complexes of transition metals with imine ligands, as described, for example, by L. K. Johnson et al. in "*Journal of the American Chemical Society*" (1995), Vol. 117, pages 6414-6415, and by G. van Koten et al. in "*Advances in Organometallic Chemistry*" (1982), Vol. 21, pages 151-239.

According to a further preferred embodiment of the present invention, said co-catalyst (b) can be selected from (b$_1$) aluminium alkyls having general formula (II):

 (II)

wherein X' represents a halogen atom such as, for example, chlorine, bromine, iodine, fluorine; R$_5$ is selected from linear or branched C$_1$-C$_{20}$ alkyl groups, cycloalkyl groups, aryl groups, said groups being optionally substituted with one or more silicon or germanium atoms; and n is an integer ranging from 0 to 2.

According to a further preferred embodiment of the present invention, said co-catalyst (b) can be selected from (b$_2$) organo-oxygenated compounds of an element M' different from carbon belonging to groups 13 or 14 of the Periodic Table of Elements, preferably organo-oxygenated compounds of aluminium, gallium, tin. Said organo-oxygenated compounds (b$_2$) can be defined as organic compounds of M', wherein the latter is bound to at least one oxygen atom and to at least one organic group consisting of an alkyl group having from 1 to 6 carbon atoms, preferably methyl.

According to a further preferred embodiment of the present invention, said co-catalyst (b) can be selected from (b$_3$) organometallic compounds or mixtures of organometallic compounds of an element M' different from carbon capable of reacting with the oxo-nitrogenated complex of cobalt having general formula (I), extracting therefrom a substituent X$_1$ or X$_2$ σ-bound, to form, on the one hand, at least one neutral compound, and on the other, an ionic compound consisting of a cation containing the metal (Co) coordinated by the ligand, and a non-coordinating organic anion containing the metal M', wherein the negative charge is delocalized on a multicentric structure.

It should be noted that, for the aim of the present invention and of the following claims, the term "Periodic Table of Elements" refers to the IUPAC version of the "Periodic Table of Elements" dated Jun. 22, 2007, provided in the following Internet website www.iupac.org/fileadmin/user_upload/news/IUPAC_Periodic_Table-1Jun12.pdf.

Specific examples of aluminium alkyls having general formula (II) which are particularly useful for the aim of the present invention are: tri-methyl-aluminium, tri-(2,3,3-tri-methyl-butyl)-aluminium, tri-(2,3-di-methyl-hexyl)-aluminium, tri-(2,3-di-methyl-butyl)-aluminium, tri-(2,3-di-methyl-pentyl)-aluminium, tri-(2,3-di-methyl-heptyl)-aluminium, tri-(2-methyl-3-ethyl-pentyl)-aluminium, tri-(2-methyl-3-ethyl-hexyl)-aluminium, tri-(2-methyl-3-ethyl-heptyl)-aluminium, tri-(2-methyl-3-propyl-hexyl)-aluminium, tri-ethyl-aluminium, tri-(2-ethyl-3-methyl-butyl)-aluminium, tri-(2-ethyl-3-methyl-pentyl)-aluminium, tri-(2,3-di-ethyl-pentyl-aluminium), tri-n-propyl-aluminium, tri-iso-propyl-aluminium, tri-(2-propyl-3-methyl-butyl)-aluminium, tri-(2-iso-propyl-3-methyl-butyl)-aluminium, tri-n-butyl-aluminium, tri-iso-butyl-aluminium (TIBA), tri-tert-butyl-aluminium, tri-(2-iso-butyl-3-methyl-pentyl)-aluminium, tri-(2,3,3-tri-methyl-pentyl)-aluminium, tri-(2,3,3-tri-methyl-hexyl)-aluminium, tri-(2-ethyl-3,3-dimethyl-butyl)-aluminium, tri-(2-ethyl-3,3-di-methyl-pentyl)-aluminium, tri-(2-iso-propyl-3,3-dimethyl-butyl)-aluminium, tri-(2-tri-methylsilyl-propyl)-aluminium, tri-2-methyl-3-phenyl-butyl)-aluminium, tri-(2-ethyl-3-phenyl-butyl)-aluminium, tri-(2,3-di-methyl-3-phenyl-butyl)-aluminium, tri-(2-phenyl-propyl)-aluminium, tri-[2-(4-fluoro-phenyl)-propyl]-aluminium, tri-[2-(4-chloro-phenyl)-propyl]-aluminium, tri-[2-(3-iso-propyl-phenyl-tri-(2-phenyl-butyl)-aluminium, tri-(3-methyl-2-phenyl-butyl)-aluminium, tri-(2-phenyl-pentyl)-aluminium, tri-[2-(penta-fluoro-phenyl)-propyl]-aluminium, tri-(2,2-diphenyl-ethyl]-aluminium, tri-(2-phenyl-methyl-propyl)-aluminium, tri-pentyl-aluminium, tri-hexyl-aluminium, tri-cyclohexyl-aluminium, tri-octyl-aluminium, di-ethyl-aluminium hydride, din-propyl-aluminium hydride, di-n-butyl-aluminium hydride, di-iso-butyl-aluminium hydride (DIBAH), di-hexyl-aluminium hydride, di-iso-hexyl-aluminium hydride, di-octyl-aluminium hydride, di-iso-octyl-aluminium hydride, ethyl-aluminium di-hydride, n-propyl-aluminium di-hydride, iso-butyl-aluminium di-hydride, di-ethyl-aluminium chloride (DEAC), mono-ethyl-aluminium dichloride (EADC), di-methyl-aluminium chloride, di-iso-butyl-aluminium chloride, iso-butyl-aluminium dichloride, ethyl-aluminium sesquichloride (EASC), and also the corresponding compounds in which one of the hydrocarbon substituents is substituted by a hydrogen atom and those in which one or two of the hydrocarbon substituents are substituted with an iso-butyl group. Di-ethyl-aluminium chloride (DEAC), mono-ethyl-aluminium dichloride (EADC), ethyl-aluminium sesquichloride (EASC), are particularly preferred.

When used for the formation of a catalytic (co)polymerization system according to the present invention, the aluminium alkyls having general formula (II) are preferably put in contact with an oxo-nitrogenated complex of cobalt having general formula (I), in such proportions that the molar ratio between the cobalt present in the oxo-nitrogenated complex of cobalt having general formula (I) and the aluminium present in the aluminium alkyls having general formula (II) can range from 5 to 5000, preferably from 10 to 1000. The sequence with which the oxo-nitrogenated complex of cobalt having general formula (I) and the aluminium alkyl having general formula (II) are put in the contact with each other, is not particularly critical.

Further details relating to the aluminium alkyls having general formula (II) can be found in international patent application WO 2011/061151.

According to a particularly preferred embodiment, said organo-oxygenated compounds ($b_2$) can be selected from aluminoxanes having general formula (III):

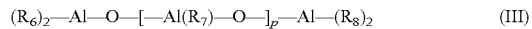

wherein $R_6$, $R_7$ and $R_8$, equal to or different from each other, represent a hydrogen atom, a halogen atom such as, for example, chlorine, bromine, iodine, fluorine; or they are selected from linear or branched $C_1$-$C_{20}$ alkyl groups, cycloalkyl groups, aryl groups, said groups being optionally substituted with one or more silicon or germanium atoms; and p is an integer ranging from 0 to 1,000.

As is known, aluminoxanes are compounds containing Al—O—Al bonds, with a variable O/Al ratio, which can be obtained by means of processes known in the art such as, for example, by reaction, under controlled conditions, of an aluminium alkyl, or an aluminium alkyl halide, with water or with other compounds containing predetermined quantities of available water, such as, for example, in the case of the reaction of aluminium trimethyl with aluminium sulfate hexahydrate, copper sulfate pentahydrate or iron sulfate pentahydrate.

Said aluminoxanes, and particularly methyl aluminoxane (MAO) are compounds which can be obtained by means of known organometallic chemical processes such as, for example, by the addition of aluminium trimethyl to a suspension in hexane of aluminium sulfate hydrate.

When used for the formation of a catalytic (co)polymerization system according to the present invention, the aluminoxanes having general formula (III) are preferably put in contact with an oxo-nitrogenated complex of cobalt having general formula (I), in such proportions that the molar ratio between the aluminium (Al) present in the aluminoxane having general formula (III) and the cobalt present in the oxo-nitrogenated complex of cobalt having general formula (I) can range from 10 to 10000, preferably from 100 to 5000. The sequence with which the oxo-nitrogenated complex of cobalt having general formula (I) and the aluminoxane having general formula (III) are put in contact with each other, is not particularly critical.

In addition to the above preferred aluminoxanes having general formula (III), the definition of the compound ($b_2$) according to the present invention can also include galloxanes, wherein, in general formula (III), gallium is present in substitution of the aluminium, and stannoxanes, wherein, in general formula (III), tin is present in substitution of the aluminium, whose use as co-catalysts in the polymerization of olefins in the presence of metallocene complexes, is known. Further details relating to said galloxanes and stannoxanes can be found, for example, in U.S. Pat. No. 5,128,295 and U.S. Pat. No. 5,258,475.

Specific examples of aluminoxanes having general formula (III) which are particularly useful for the aim of the present invention are: methylaluminoxane (MAO), ethyl-aluminoxane, n-butyl-aluminoxane, tetra-iso-butyl-aluminoxane (TIBAO), tert-butyl-aluminoxane, tetra-(2,4,4-tri-methyl-pentyl)-aluminoxane (TIOAO), tetra-(2,3-di-methyl-butyl)-aluminoxane (TDMBAO), tetra-(2,3,3-tri-methyl-butyl)-aluminoxane (TTMBAO). Methylaluminoxane (MAO) is particularly preferred.

Further details relating to the aluminoxanes having general formula (III) can be found in international patent application WO 2011/061151.

According to a preferred embodiment of the present invention, said compounds or mixtures of compounds ($b_3$) can be selected from organic compounds of aluminium and especially boron, such as, for example, those represented by the following general formulae:

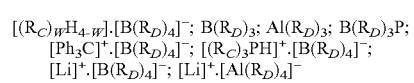

wherein w is an integer ranging from 0 to 3, each group $R_C$ independently represents an alkyl group or an aryl group having from 1 to 10 carbon atoms and each group $R_D$ independently represents an aryl group partially or totally, preferably totally, fluorinated, having from 6 to 20 carbon atoms, P represents a pyrrole radical optionally substituted.

When used for the formation of a catalytic (co)polymerization system according to the present invention, the compounds or mixtures of compounds ($b_3$) may be preferably put in contact with an oxo-nitrogenated complex of cobalt having general formula (I), in such proportions that the molar ratio between the metal (M') present in the compounds or mixtures of compounds ($b_3$) and the cobalt present in the oxo-nitrogenated complex of cobalt having general formula (I) ranges from 0.1 to 15, preferably from 0.5 to 10, more preferably from 1 to 6. The sequence with which the oxo-nitrogenated complex of cobalt having general formula (I) and the compound or mixture of compounds ($b_3$) are put in contact with each other, is not particularly critical.

Said compounds or mixtures of compounds ($b_3$), especially when $X_1$ and $X_2$ in the oxo-nitrogenated complex of cobalt having general formula (I) are different from alkyl, must be used in a combination with an aluminoxane having general formula (III) such as, for example, methylaluminoxane (MAO), or, preferably, with an aluminium alkyl having general formula (II), more preferably an aluminium trialkyl having from 1 to 8 carbon atoms in each alkyl residue such as, for example, tri-methyl-aluminium, tri-ethyl-aluminium, tri-iso-butylaluminium (TIBA).

Examples of the methods generally used for the formation of a catalytic (co)polymerization system according to the present invention, when compounds or mixtures of compounds ($b_3$) are used, are qualitatively schematized in the following list, which however in no way limits the overall scope of the present invention:

($m_1$) contact of an oxo-nitrogenated complex of cobalt having general formula (I) wherein at least one of $X_1$ and $X_2$ is an alkyl group, with at least one compound or mixture of compounds ($b_3$) whose cation is capable of reacting with said alkyl group to form a neutral compound, and whose anion is voluminous, non-coordinating and capable of delocalizing the negative charge;

($m_2$) reaction of an oxo-nitrogenated complex of cobalt having general formula (I) with at least one aluminium alkyl having general formula (II), preferably an aluminium trialkyl, used in a molar excess of 10/1 to 300/1, followed by reaction with a strong Lewis acid, such as, for example, tris(pentafluorophenyl)boron [compound ($b_3$)], in an almost stoichiometric quantity or in slight excess with respect to the cobalt (Co);

($m_3$) contact and reaction of an oxo-nitrogenated complex of cobalt having general formula (I) with a molar excess of 10/1 to 1000/1, preferably from 100/1 to 500/1, of at least one aluminium trialkyl or an alkyl aluminium halide represented by the formula $AlR'''_m Z_{3-m}$ wherein $R'''$ is a linear or branched $C_1$-$C_8$ alkyl group, or a mixture thereof, Z is a halogen, preferably chlorine or bromine, and m is a decimal number ranging from 1 to 3, followed by addition, to the composition thus obtained, of at least one compound or mixture of compounds ($b_3$) in such quantities that the ratio between said compound or mixture of compounds ($b_3$) or the aluminium of said compound or mixture of compounds ($b_3$) and the cobalt of the oxo-nitrogenated complex of cobalt having general formula (I) ranges from 0.1 to 15, preferably from 1 to 6.

Examples of compounds or mixtures of compounds ($b_3$) capable of producing an ionic catalytic system by reaction with an oxo-nitrogenated complex of cobalt having general formula (I) according to the present invention, are described, although with reference to the formation of ionic metallocene complexes, in the following publications, whose contents are incorporated herein as reference:

W. Beck et al., "*Chemical Reviews*" (1988), Vol. 88, pages 1405-1421;

S. H. Stares, "*Chemical Reviews*" (1993), Vol. 93, pages 927-942;

European patent applications EP 277 003, EP 495 375, EP 520 732, EP 427 697, EP 421 659, EP 418044;

published international patent applications WO 92/00333, WO 92/05208.

Specific examples of compounds or mixtures of compounds ($b_3$) particularly useful for the aim of the present invention are: tributylammonium-tetrakis-pentafluorophenyl-borate tributylammonium-tetrakis-pentafluorophenyl-aluminate, tributylammonium-tetrakis-[(3,5-di-(trifluorophenyl)]-borate, tributylammonium-tetrakis-(4-fluorophenyl)]-borate, N,N-dimethylbenzyl-ammonium-tetrakis-pentafluoro-phenyl-borate, N,N-di-methyl-hexylammonium-tetrakis-pentafluorophenyl-borate, N,N-dimethylanilinium-tetrakis-(pentafluorophenyl)-borate, N,N-dimethylanilinium-tetrakis-(pentafluoro-phenyl)-aluminate, di-(propyl)-ammonium-tetrakis-(pentafluorophenyl)-borate, di-(cyclohexyl)-ammonium-tetrakis-(pentafluorophenyl)-borate, tri-phenyl-carbenium-tetrakis-(pentafluorophenyl)-borate, tri-phenylcarbenium-tetrakis-(penta-fluorophenyl)-aluminate, tris(pentafluorophenyl)boron, tris(penta-fluorophenyl)-aluminium, or mixtures thereof. Tetrakis-pentafluorophenyl-borates are preferred.

For the aim of the present description and of the following claims, the term "mole" and "molar ratio" are used with reference to compounds consisting of molecules and also with reference to atoms and ions, omitting, for the latter, the terms gram atom or atomic ratio, even if scientifically more correct.

For the aim of the present invention, other additives or components can be optionally added to the above catalytic system in order to adapt it so as to satisfy specific practical requirements. The catalytic systems thus obtained should therefore be considered as being included in the scope of the present invention. Additives and/or components which can be added in the preparation and/or formulation of the above catalytic system, object of the present invention, are, for example: inert solvents, such as, for example, aliphatic and/or aromatic hydrocarbons, aliphatic and/or aromatic ethers, weakly coordinating additives (e.g. Lewis bases) selected, for example, from non-polymerizable olefins, sterically hindered or electronically poor ethers, halogenating agents such as, for example, silicon halides, halogenated hydrocarbons, preferably chlorinated; or mixtures thereof.

As already specified above, said catalytic system can be prepared according to methods known in the art.

Said catalytic system, for example, can be prepared separately (preformed) and subsequently introduced into the (co)polymerization environment. In this respect, said catalytic system can be prepared by reacting at least one oxo-nitrogenated complex of cobalt (a) having general formula (I) with at least one co-catalyst (b), optionally in the presence of other additives or components selected from those listed above, in the presence of a solvent such as, for example, toluene, heptane, at a temperature ranging from 20° C. to 60° C., for a time ranging from 10 seconds to 10 hours, preferably from 30 seconds to 5 hours. Further details on the preparation of said catalytic system can be found in the examples provided hereunder.

Alternatively, said catalytic system can be prepared in situ, i.e. directly in the (co)polymerization environment. In this respect, said catalytic system can be prepared by introducing the oxo-nitrogenated complex of cobalt (a) having general formula (I), the co-catalyst (b) and the preselected conjugated diene(s) to be (co)polymerized, separately, operating under the conditions in which the (co)polymerization is carried out.

For the aim of the present invention, the above catalytic systems can also be supported on inert solids, preferably consisting of silicon and/or aluminium oxides, such as, for example, silica, alumina or silico-aluminates. The known supporting techniques can be used for supporting said catalytic systems, generally comprising contact, in a suitable inert liquid medium, between the carrier, optionally activated by heating to temperatures higher than 200° C., and one or both of components (a) and (b) of the catalytic system, object of the present invention. For the aim of the present invention, it is not necessary for both components to be supported, as the oxo-nitrogenated complex of cobalt (a) having general formula (I) alone, or the co-catalyst (b) alone, can be present on the surface of the carrier. In the latter case, the missing component on the surface is subsequently put in contact with the supported component, at the moment in which the catalyst active for the polymerization is to be formed.

The oxo-nitrogenated complex of cobalt having general formula (I), and the catalytic systems based thereon, which have been supported on a solid by the functionalization of the latter and formation of a covalent bond between the solid and oxo-nitrogenated complex of cobalt having general formula (I), are also included in the scope of the present invention.

The present invention also relates to a process for the (co)polymerization of conjugated dienes, characterized by the use of said catalytic system.

The quantity of oxo-nitrogenated complex of cobalt (a) having general formula (I) and of co-catalyst (b) that can be used in the (co)polymerization of conjugated dienes varies according to the (co)polymerization process to be carried out. Said quantity is in any case such as to obtain a molar ratio between the cobalt present in the oxo-nitrogenated complex of cobalt having general formula (I) and the metal present in the co-catalyst (b), e.g., aluminium when the co-catalyst (b) is selected from aluminium alkyls ($b_1$) or aluminoxanes ($b_2$), boron when the co-catalyst (b) is selected from compounds or mixtures of compounds ($b_3$) having general formula (III), included within the values indicated above.

Specific examples of conjugated dienes that can be (co)polymerized using the catalytic system according to the present invention are: 1,3-butadiene, 2-methyl-1,3-butadiene (isoprene), 2,3-dimethyl-1,3-butadiene, 1,3-pentadiene, 1,3-hexadiene, cyclo-1,3-hexadiene. Preferred (co)polymerizable conjugated dienes are 1,3-butadiene, isoprene. The above (co)polymerizable conjugated dienes can be used alone, or in a mixture of two or more dienes. In the latter case, i.e. using a mixture of two or more dienes, a copolymer is obtained.

According to a particularly preferred embodiment, the present invention relates to a process for the polymerization of 1,3-butadiene or isoprene, characterized by the use of said catalytic system.

Said (co)polymerization process can generally be carried out in the presence of a polymerization solvent, generally selected from inert organic solvents such as, for example: saturated aliphatic hydrocarbons such as, for example, butane, pentane, hexane, heptane, or mixtures thereof; saturated cycloaliphatic hydrocarbons such as, for example, cyclopentane, cyclohexane, or mixtures thereof; mono-olefins such as, for example, 1-butene, 2-butene, or mixtures thereof; aromatic hydrocarbons such as, for example, benzene, toluene, xylene, or mixtures thereof; halogenated hydrocarbons such as, for example, methylene chloride, chloroform, carbon tetrachloride, trichloroethylene, perchloroethylene, 1,2-dichloroethane, chlorobenzene, bromobenzene, chlorotoluene, or mixtures thereof. The (co)polymerization solvent is preferably selected from saturated aliphatic hydrocarbons.

Alternatively, said (co)polymerization can be carried out using, as (co)polymerization solvent, the same conjugated diene(s) to be (co)polymerized, according to the process known as "bulk process".

The concentration of conjugated diene to be (co)polymerized in said (co)polymerization solvent generally ranges from 5% by weight to 50% by weight, preferably from 10% by weight to 20% by weight, with respect to the total weight of the mixture of conjugated diene and inert organic solvent.

Said (co)polymerization process can generally be carried out at a temperature ranging from −70° C. to +100° C., preferably from −20° C. to +80° C.

As far as the pressure is concerned, it is preferable to operate at the pressure of the components of the mixture to be (co)polymerized.

Said (co)polymerization can be carried out either in continuous or batchwise.

As indicated above, said process allows (co)polymers of conjugated dienes to be obtained, such as, for example, polybutadiene, polyisoprene, in particular, linear or branched polybutadiene, with a high content of 1,4-cis units, i.e. a content of 1,4-cis units ≥96%.

Some illustrative and non-limiting examples are provided hereunder for a better understanding of the present invention and for its practical embodiment.

EXAMPLES

Reagents and Materials

The reagents and materials used in the following examples of the invention are indicated in the following list, together with their optional e pre-treatments and their supplier:

aniline (Aldrich): distilled at reduced pressure and preserved in an inert atmosphere;
cobalt dichloride ($CoCl_2$) (Stream Chemicals); used as such;
tetrahydrofuran (THF) (Carlo Erba, RPE): kept at reflux temperature on potassium/benzophenone and then distilled under nitrogen;
methanol (Carlo Erba, RPE): used as such;
p-toluidine (Aldrich): distilled at reduced pressure and preserved in an inert atmosphere;
2,4-pentandione (Aldrich): used as such;
toluene (Aldrich): pure, ≥99.5%, distilled on sodium (Na) in an inert atmosphere;
1,3-butadiene (Air Liquide): pure, ≥99.5%, evaporated from the container before each production, dried by passing it through a column packed with molecular sieves and condensed inside the reactor pre-cooled to −20° C.;
methylaluminoxane (MAO) (toluene solution at 10% by weight) (Aldrich): used as such;
heptane (Aldrich): pure, ≥99%, distilled on sodium (Na) in an inert atmosphere;
pentane (Aldrich): pure, ≥99%, distilled on sodium (Na) in an inert atmosphere;
hexane (Aldrich): pure, ≥99%, distilled on sodium (Na) in an inert atmosphere;
deuterated tetrachloroethylene ($C_2D_2Cl_4$) (Acros): used as such;
deuterated chloroform ($CDCl_3$) (Acros): used as such;
ethylenediamine (Aldrich): used as such;

hydrochloric acid in aqueous solution at 37% (Aldrich): used as such.

The analysis and characterization methods indicated below were used.

Elemental Analysis a) Determination of Co

For the determination of the weight quantity of cobalt (Co) in the oxo-nitrogenated complexes of cobalt used for the aim of the present invention, an aliquot weighed exactly, operating in a dry-box under a nitrogen flow, of about 30-50 mg of sample, was placed in a platinum crucible of about 30 ml, together with a mixture of 1 ml of hydrofluoric acid (HF) at 40%, 0.25 ml of sulfuric acid ($H_2SO_4$) at 96% and 1 ml of nitric acid ($HNO_3$) at 70%. The crucible was then heated on a plate, increasing the temperature until the appearance of white sulfuric fumes (about 200° C.). The mixture thus obtained was cooled to room temperature (20° C.-25° C.), 1 ml of nitric acid ($HNO_3$) at 70% was added and the mixture was then heated until the re-appearance of fumes. After repeating the sequence a further two times, a limpid, almost colourless solution was obtained. 1 ml of nitric acid ($HNO_3$) and about 15 ml of water were then added, without heat, and the mixture was then heated to 80° C. for about 30 minutes. The sample thus prepared was diluted with water having a MilliQ purity up to a weight of about 50 g, weighed exactly, to obtain a solution on which analytical instrumental determination was carried out using an ICP-OES (optical detection plasma) Thermo Optek IRIS Advantage Duo spectrometer, by comparison with solutions at a known concentration. For this aim, a calibration curve was prepared for each analyte, within the range of 0 ppm-10 ppm, measuring solutions having a known titre obtained by dilution by weight of certified solutions.

The solution of the sample prepared as described above was diluted again by weight so as to obtain concentrations close to those used as reference, before carrying out spectrophotometric detection. All the samples were prepared in duplicate. The results were considered acceptable if the single data of the tests in duplicate did not differ by more than 2% relative with respect to their average value.

b) Chlorine Determination

For this aim, samples of the oxo-nitrogenated complexes of cobalt used for the aim of the present invention, about 30 mg-50 mg, were weighed exactly in 100 ml glasses in a dry-box under a stream of nitrogen. 2 g of sodium carbonate ($Na_2CO_3$) and 50 ml of MilliQ water were added, outside the dry-box. The mixture was brought to boiling point on a plate under magnetic stirring for about 30 minutes. It was left to cool, diluted sulfuric acid ($H_2SO_4$) 1/5 was added until the reaction became acid and the mixture was titrated with silver nitrate ($AgNO_3$) 0.1N with a potentiometer titrator.

c) Determination of Carbon, Hydrogen, Nitrogen and Oxygen

The determination of the carbon, hydrogen, nitrogen and oxygen in the oxo-nitrogenated complexes of cobalt, used for the aim of the present invention, and also in the ligands used for the aim of the present invention, was carried out by means of a Carlo Erba Mod. 1106 automatic analyzer.

$^{13}C$-HMR and $^1H$-HMR spectra

The $^{13}C$-HMR and $^1H$-HMR spectra were registered by means of a nuclear magnetic resonance spectrometer mod. Bruker Avance 400, using deuterated tetrachloroethylene ($C_2D_2Cl_4$) at 103° C., and hexamethyldisiloxane (HDMS) as internal standard, or using deuterated chloroform ($CDCl_3$) at 25° C., and tetramethylsilane (TMS) as internal standard. Polymeric solutions having concentrations equal to 10% by weight with respect to the total weight of the polymeric solution, were used for the aim.

The microstructure of the polymers [i.e. content of 1,4-cis units (%)] was determined by analysis of the above spectra on the basis of what is indicated in literature by Mochel, V. D., in "Journal of Polymer Science Part A-1: Polymer Chemistry" (1972), Vol. 10, Issue 4, pages 1009-1018.

I.R. Spectra

The I.R. spectra (FT-IR) were registered by means of Thermo Nicolet Nexus 670 and Bruker IFS 48 spectrophotometers.

The I.R. spectra (FT-IR) of the ligands used in the present invention, were obtained by dispersing the ligand to be analyzed in anhydrous potassium bromide (KBr) (disks of KBr), or in a suspension of nujol.

The I.R. spectra (FT-IR) of the oxo-nitrogenated complexes of cobalt used in the present invention, were obtained by dispersing the oxo-nitrogenated complex of cobalt to be analyzed in anhydrous potassium bromide (KBr) (disks of KBr), or in a suspension of nujol.

The I.R. spectra (FT-IR) of the polymers were obtained from polymeric films on tablets of potassium bromide (KBr), said films being obtained by deposition of a solution of the polymer to be analyzed in hot o-dichlorobenzene. The concentration of the polymeric solutions analyzed was equal to 10% by weight with respect to the total weight of the polymeric solution.

Thermal Analysis (DSC)

The DSC ("Differential Scanning calorimetry") thermal analysis, for determining the melting point ($T_m$) and crystallization temperature ($T_c$) of the polymers obtained, was carried out using a Perkin Elmer Pyris differential scanning calorimeter. For this aim, 5 mg of polymer were analyzed, with a scanning rate ranging from 1° C./min to 20° C./min, in an inert nitrogen atmosphere.

The DSC ("Differential Scanning calorimetry") thermal analysis, for determining the glass transition temperature ($T_g$) of the polymers obtained was carried out by means of the above calorimeter, using the following thermal program: isotherm for 3 minutes at +70° C.; cooling from +70° C. to −90° C. at a rate of 10° C./min; isotherm for 3 min at −90° C.; heating from −90° C. to +70° C. at a rate of 10° C./min.

Molecular Weight Determination

The determination of the molecular weight (MW) of the polymers obtained was carried out by means of GPC ("Gel Permeation Chromatography") operating under the following conditions:

Agilent 1100 pump;
I.R. Agilent 1100 detector;
PL Mixed-A columns;
solvent/eluent: tetrahydrofuran (THF);
flow-rate: 1 ml/min;
temperature: 25° C.;
molecular mass calculation: Universal Calibration method.

The weight average molecular weight ($M_w$) and polydispersion Index" (PDI) corresponding to the $M_w/M_n$ ratio ($M_n$=number average molecular weight), are specified.

Determination of the Branching

The determination of the branching of the polymers obtained was carried out by means of the GPC/MALLS technique obtained by coupling a multi-angle light scattering detector (MALLS) with a traditional SEC/RI elution, operating under the following conditions:

Agilent 1050 pump;
I.R. Agilent 1050 detector;

MALLS Dawn-DSP Wyatt detector—Technology, λ=632.8 nm;
PL GEL Mixed-A (×4) columns;
solvent/eluent: tetrahydrofuran (THF);
flow-rate: 1 ml/min;
temperature: 25° C.

Operating as described above, the absolute measurement can be contemporaneously carried out of the molecular weight and gyration radius of the macromolecules that are separated by the chromatographic system: the quantity of light scattered from a macromolecular species in solution can in fact be used directly for obtaining its molecular weight, whereas the angular variation in the scattering is directly correlated to its average dimensions. The fundamental relation which is used is represented by the following equation (1):

$$\frac{K*c}{R_\theta} = \frac{1}{M_w P_\theta} + 2A_2 c \quad (1)$$

wherein:
K* is the optical constant which depends on the wavelength of the light used, on the refraction index (dn/dc) of the polymer, on the solvent used;
$M_w$ is the weight average molecular weight;
c is the concentration of the polymeric solution;
$R_\theta$ is the intensity of the light scattered, measured at the angle θ (excess Rayleigh factor);
$P_\theta$ is the function describing the variation of the light scattered with the angle at which it is measured, equal to 1 for an angle θ equal to 0;
$A_2$ is the second virial coefficient.

For very low concentrations (typical of a GPC system), the equation (1) indicated above is reduced to the following equation (2):

$$\frac{K*c}{R_\theta} = \frac{1}{M_w P_\theta} \quad (2)$$

wherein K*, c, $R_\theta$, $M_w$ and $P_\theta$, have the same meanings defined above, and by carrying out the measurement on several angles, the extrapolation at angle null of the function $K*c/R_\theta$ in relation to $sen^2\theta/2$ directly provides the molecular weight of the intercept value and the gyration radius of the slope.

Furthermore, as this measurement is carried out for every slice of the chromatogram, it is possible to obtain a distribution of both the molecular weight and gyration radius.

The macromolecular dimensions in solution are directly correlated to their branching degree: for the same molecular weight, the smaller the dimensions of the macromolecule with respect to the linear correspondent, the higher the branching degree will be.

Information relating to the macrostructure of the polymer is qualitatively deduced from the value of the parameter α, which represents the slope of the curve which correlates the gyration radius with the molecular weight: when, under the same analysis conditions, this value decreases with respect to a macrostructure of the linear type, there is the presence of a polymer having a branched-type macrostructure. The typical value of the parameter α for linear polybutadiene having a high content of 1,4-cis units, in tetrahydrofuran (THF), is equal to 0.58-0.60.

Example 1

Synthesis of the Ligand Having Formula (L1)

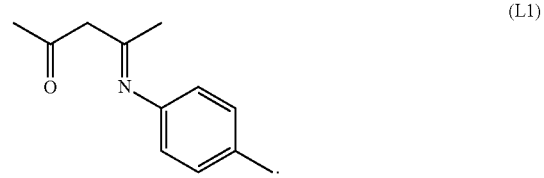

(L1)

5 g (50 mmoles) of 2,4-pentandione were introduced into a reaction flask equipped with a Dean-Stark trap for the azeotropic removal of the water, together with 75 ml of benzene, a few drops of hydrochloric acid and 5.5 g (51 mmoles) of p-toluidine: the mixture obtained was heated to reflux temperature, under nitrogen, for 24 hours. The mixture was then cooled to room temperature, filtered on a porous septum, obtaining a filtrate which was evaporated under vacuum, obtaining a yellow-orange oil. The oil thus obtained was dissolved in ethyl ether (10 ml) and put in a freezer for 24 hours, obtaining a solid product which was filtered and dried, under vacuum, at room temperature, obtaining 6.1 g of a yellowish solid product (yield=64.5%) having formula (L1).

Elemental analysis [found (calculated)]: C: 75.74% (76.16%); H: 7.98% (7.99%); N: 7.31% (7.40%); O: 8.71% (8.45%).

Molecular weight (MW): 189.25.

FT-IR (nujol): 1610 cm$^{-1}$ $v_{(C=O)}$; 1570 cm$^{-1}$ $v_{(C=N)}$.

Example 2

Synthesis of the Ligand Having Formula (L4)

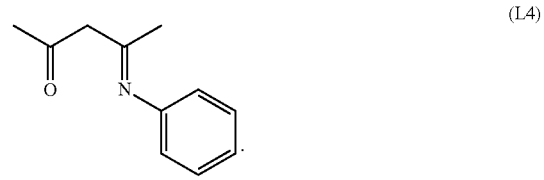

(L4)

5 g (50 mmoles) of 2,4-pentandione were introduced into a reaction flask equipped with a Dean-Stark trap for the azeotropic removal of the water, together with 75 ml of benzene, a few drops of hydrochloric acid and 4.66 g (50 mmoles) of aniline: the mixture obtained was heated to reflux temperature, under nitrogen, for 24 hours. The mixture was then cooled to room temperature, filtered on a porous septum, obtaining a filtrate which was evaporated under vacuum, obtaining an orange oil. The oil thus obtained was dissolved in ethyl ether (10 ml) and put in a freezer for 24 hours, obtaining a solid product which was filtered and dried, under vacuum, at room temperature, obtaining 4.3 g of a yellowish solid product (yield=62%) having formula (L4).

Elemental analysis [found (calculated)]: C: 75.20% (75.40%); H: 7.50% (7.48%); N: 8.0% (7.99%); O: 9.12% (9.13%).

Molecular weight (MW): 175.23.

FT-IR (nujol): 1620 cm$^{-1}$ $v_{(C=O)}$; 1577 cm$^{-1}$ $v_{(C=N)}$.

Example 3

Synthesis of the Ligand Having Formula (L6)

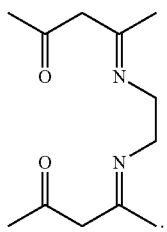
(L6)

6 g (100 mmoles) of ethylenediamine were introduced into a reaction flask together with 20 ml of 2,4-pentandione: the mixture obtained was kept under stirring, at room temperature, for 6 hours. The mixture was then put in a freezer, obtaining the precipitation of a white solid product which was re-crystallized from water, washed with water and dried, under vacuum, at room temperature, obtaining 22 g of a white solid product (yield=98%) having formula (L6).

Elemental analysis [found (calculated)]: C: 64.30% (64.26%); H: 8.91% (8.99%); N: 12.60% (12.49%); O: 14.0% (14.27%).

Molecular weight (MW): 224.3.

FT-IR (nujol): 1606 cm$^{-1}$ $v_{(C=O)}$; 1575 cm$^{-1}$ $v_{(C=N)}$.

Example 4

Synthesis of CoCl$_2$(L1) [Sample GL770]

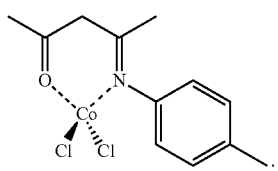
(GL770)

Anhydrous cobalt dichloride (CoCl$_2$) (0.397 g; 3.06 mmoles) was introduced into a 100 ml reaction flask together with tetrahydrofuran (THF) (50 ml). The whole was kept under stirring, at room temperature, for a few minutes and the ligand having formula (L1) (0.681 g; 3.6 mmoles; molar ratio L1/Co=1.2) obtained as described in Example 1, was subsequently added. Upon the addition of the ligand, a dark blue-coloured suspension was immediately formed, which was kept, under stirring, at room temperature, for 1 day. The solvent was then removed under vacuum and the residue obtained was dried under vacuum, at room temperature, and subsequently charged onto the porous septum of a hot extractor for solids and was extracted, in continuous, with pentane at boiling point, for 24 hours, in order to remove the non-reacted ligand. Subsequently, the residue remaining on the porous septum was extracted again, in continuous, with dichloromethane at boiling point for 24 hours, obtaining a green-coloured solution. The dichloromethane was removed under vacuum and the solid residue remaining on the porous septum was recovered and dried under vacuum, at room temperature, obtaining 0.89 g of a dark green solid product corresponding to the complex CoCl$_2$(L1), equal to a conversion of 91.4% with respect to the cobalt dichloride charged.

Elemental analysis [found (calculated)]: C: 44.60% (45.17%); H: 4.20% (4.74%); Cl: 21.70% (22.22%); Co: 18.10% (18.47%); N: 4.20% (4.39%); O: 4.90% (5.01%).

Molecular weight (MW): 319.09

FT-IR (nujol): 1591 cm$^{-1}$ $v_{(C=O)}$; 1555 cm$^{-1}$ $v_{(C=N)}$.

Example 5

Synthesis of CoCl$_2$(L4) [Sample GL924]

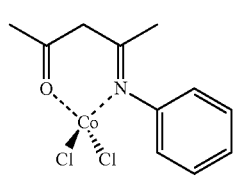
(GL924)

Anhydrous cobalt dichloride (CoCl$_2$) (0.415 g; 3.2 mmoles) was introduced into a 100 ml reaction flask together with tetrahydrofuran (THF) (70 ml). The whole was kept under stirring, at room temperature, for a few minutes and the ligand having formula (L4) (0.615 g; 3.51 mmoles; molar ratio L4/Co=1.1) obtained as described in Example 2, was subsequently added. Upon the addition of the ligand, an indigo-coloured suspension was immediately formed, which was kept, under stirring, at room temperature, for 1 day. The solvent was then removed under vacuum and the residue obtained was dried under vacuum, at room temperature, and subsequently charged onto the porous septum of a hot extractor for solids and was extracted, in continuous, with pentane at boiling point, for 24 hours, in order to remove the non-reacted ligand. The residue remaining on the porous septum was subsequently recovered and dried under vacuum, at room temperature, obtaining 0.87 g of an indigo solid product corresponding to the complex CoCl$_2$(L4), equal to a conversion of 89.1% with respect to the cobalt dichloride charged.

Elemental analysis [found (calculated)]: C: 42.90% (43.31%); H: 4.20% (4.30%); Cl: 22.90% (23.24%); Co: 18.90% (19.32%); N: 4.20% (4.59%); O: 5.0% (5.24%).

Molecular weight (MW): 305.07

FT-IR (nujol): 1603 cm$^{-1}$ $v_{(C=O)}$; 1551 cm$^{-1}$ $v_{(C=N)}$.

FIG. 1 shows the FT-IR spectrum of the complex CoCl$_2$(L4) obtained (the nujol bands having been subtracted).

Example 6

Synthesis of CoCl$_2$(L6) [Sample GL927]

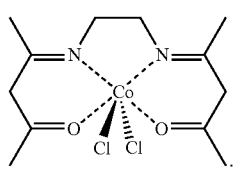
(GL927)

Anhydrous cobalt dichloride (CoCl$_2$) (0.830 g; 6.39 mmoles) was introduced into a 100 ml reaction flask together with tetrahydrofuran (THF) (70 ml). The whole was kept under stirring, at room temperature, for a few minutes and the ligand having formula (L6) (1.57 g; 7 mmoles; molar ratio L6/Co=1.1) obtained as described in Example 3, was subsequently added. Upon the addition of the ligand, a light-blue-coloured suspension was immediately formed, which was kept, under stirring, at room temperature, for 1 day. The solvent was then removed under vacuum and the residue obtained was dried under vacuum, at room temperature, and subsequently charged onto the porous septum of a hot extractor for solids and was extracted, in continuous, with pentane at boiling point, for 24 hours, in order to remove the non-reacted ligand. The residue remaining on the porous septum was subsequently recovered and dried under vacuum, at room temperature, obtaining 1.81 g of a light blue solid product corresponding to the complex $CoCl_2(L6)$, equal to a conversion of 80% with respect to the cobalt dichloride charged.

Elemental analysis [found (calculated)]: C: 40.40% (40.70%); H: 5.40% (5.69%); Cl: 19.80% (20.02%); Co: 16.40% (16.64%); N: 7.60% (7.91%); O: 8.90% (9.04%).

Molecular weight (MW): 354.14

FT-IR (nujol): 1606 cm$^{-1}$ $\nu_{(C=O)}$; 1575 cm$^{-1}$ $\nu_{(C=N)}$.

Figure 2:
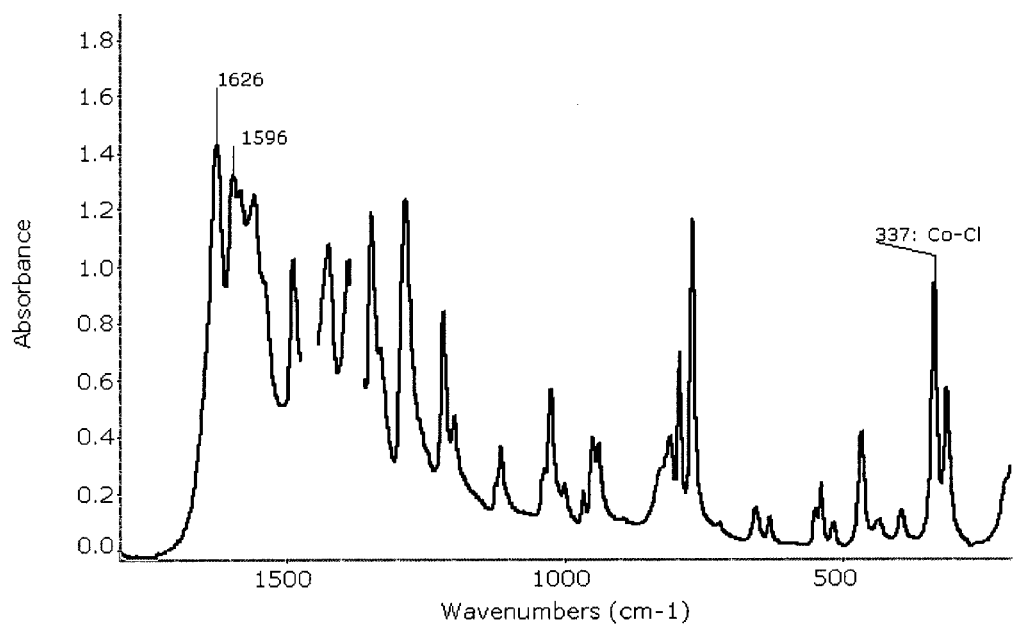
FIG. 2: FT-IR spectrum of the CoCl2(L6)complex [sample GL927] (Example 6) (the nujol bands have been subtracted)

FIG. 2 shows the FT-IR spectrum of the complex $CoCl_2$(L6) obtained (the nujol bands having been subtracted).

Example 7

GL780

2 ml of 1,3-butadiene equal to about 1.4 g were condensed at a low temperature (−20° C.) in a 25 ml test-tube. 8.1 ml of toluene were then added, and the temperature of the solution thus obtained was brought to 20° C. Methylaluminoxane (MAO) in a toluene solution (6.3 ml; 1×10$^{-2}$ moles, equal to about 0.58 g) was then added, and subsequently the complex $CoCl_2$(L1) [sample GL770] (1.6 ml of a toluene solution at a concentration equal to 2 mg/ml; 1×10$^{-5}$ moles, equal to about 3.2 mg) obtained as described in Example 4. The whole was kept, under magnetic stirring, at 20° C., for 35 minutes. The polymerization was then quenched by the addition of 2 ml of methanol containing a few drops of hydrochloric acid. The polymer obtained was then coagulated by the addition of 40 ml of a methanol solution containing 4% of Irganox® 1076 antioxidant (Ciba), obtaining 1.15 g of polybutadiene having a content of 1,4-cis units equal to 98%: further characteristics of the process and polybutadiene obtained are indicated in Table 1.

Figure 3:
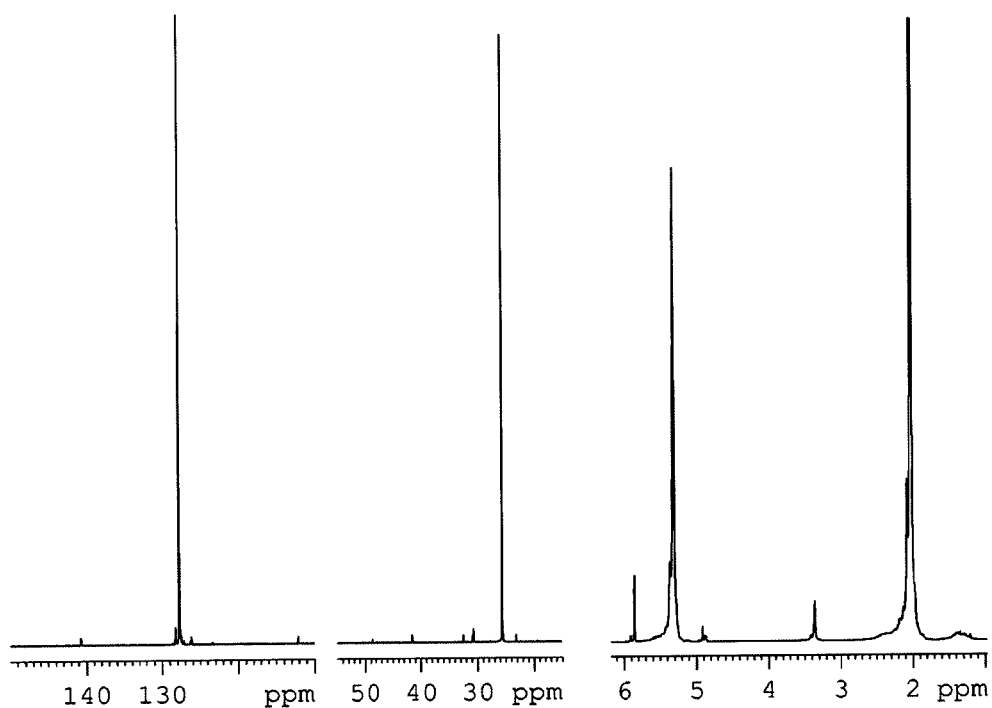
FIG. 3: $^{13}$C-NMR spectrum (on the left) and $^1$H-NMR spectrum (on the right) of the polybutadiene of Example 7.

FIG. 3 shows the $^1$H-NMR and $^{13}$C-NMR spectra of the polybutadiene obtained.

Example 8

GL815

2 ml of 1,3-butadiene equal to about 1.4 g were condensed at a low temperature (−20° C.) in a 25 ml test-tube. 8.1 ml of toluene were then added, and the temperature of the solution thus obtained was brought to 50° C. Methylaluminoxane (MAO) in a toluene solution (6.3 ml; 1×10$^{-2}$ moles, equal to about 0.58 g) was then added, and subsequently the complex $CoCl_2$(L1) [sample GL770] (1.6 ml of a toluene solution at a concentration equal to 2 mg/ml; 1×10$^{-5}$ moles, equal to about 3.2 mg) obtained as described in Example 4. The whole was kept, under magnetic stirring, at 50° C., for 10 minutes. The polymerization was then quenched by the addition of 2 ml of methanol containing a few drops of hydrochloric acid. The polymer obtained was then coagulated by the addition of 40 ml of a methanol solution containing 4% of Irganox® 1076 antioxidant (Ciba), obtaining 0.94 g of polybutadiene having a content of 1,4-cis units equal to 97.3%: further characteristics of the process and polybutadiene obtained are indicated in Table 1.

Example 9

GL980/1

2 ml of 1,3-butadiene equal to about 1.4 g were condensed at a low temperature (−20° C.) in a 25 ml test-tube. 8.1 ml of heptane were then added, and the temperature of the solution thus obtained was brought to 50° C. Methylaluminoxane (MAO) in a toluene solution (6.3 ml; 1×10$^{-2}$ moles, equal to about 0.58 g) was then added, and subsequently the complex $CoCl_2$(L1) [sample GL770] (1.6 ml of a toluene solution at a concentration equal to 2 mg/ml; 1×10$^{-5}$ moles, equal to about 3.2 mg) obtained as described in Example 4. The whole was kept, under magnetic stirring, at 50° C., for 10 minutes. The polymerization was then quenched by the addition of 2 ml of methanol containing a few drops of hydrochloric acid. The polymer obtained was then coagulated by the addition of 40 ml of a methanol solution containing 4% of Irganox® 1076 antioxidant (Ciba), obtaining 0.98 g of polybutadiene having a content of 1,4-cis units equal to 96.7%: further characteristics of the process and polybutadiene obtained are indicated in Table 1.

Figure 4:
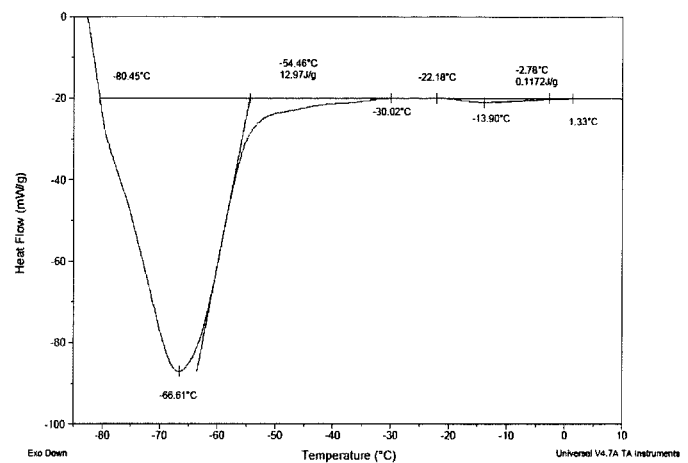
FIG. 4: DSC diagrams of the polybutadiene of Example 9: (A) crystallization; (B) melting.
Figure 4:
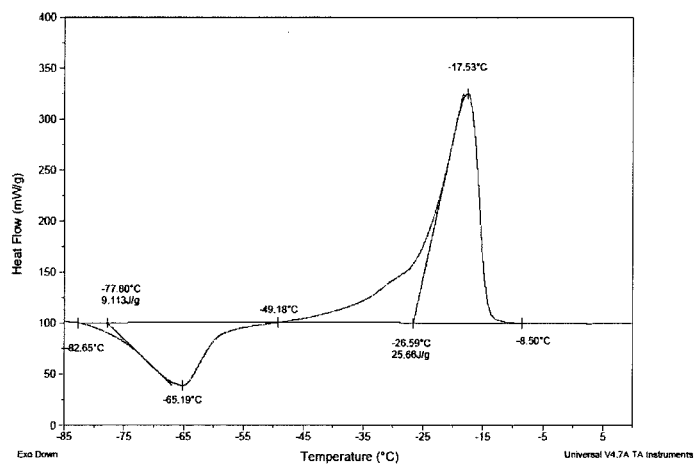

FIG. 4 shows the DSC diagrams of the polybutadiene obtained.

Figure 5:
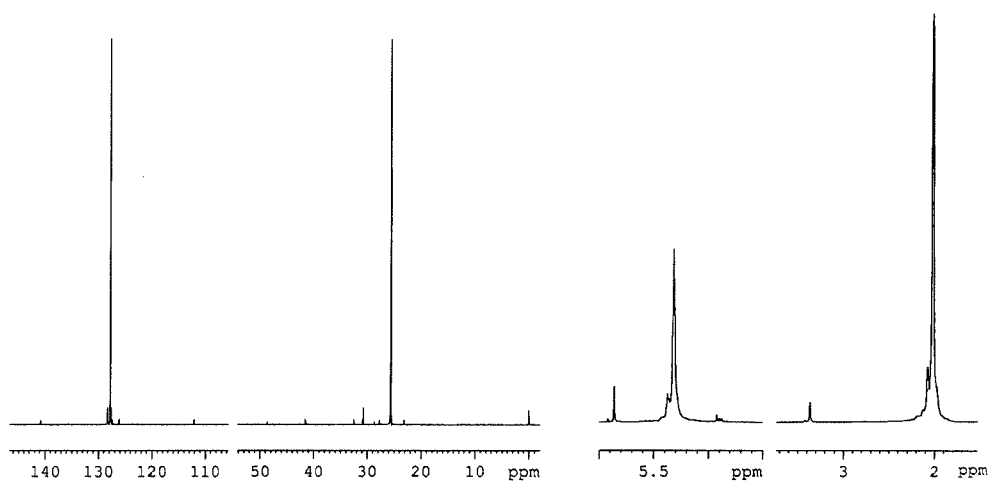
FIG. 5: $^{13}$C-NMR spectrum (on the left) and $^1$H-NMR spectrum (on the right) of the polybutadiene of Example 9.

FIG. 5 shows the $^1$H-NMR and $^{13}$C-NMR spectra of the polybutadiene obtained.

Example 10

GL968

2 ml of 1,3-butadiene equal to about 1.4 g were condensed at a low temperature (−20° C.) in a 25 ml test-tube. 8.1 ml of toluene were then added, and the temperature of the solution thus obtained was brought to 20° C. Methylaluminoxane (MAO) in a toluene solution (6.3 ml; 1×10$^{-2}$ moles, equal to about 0.58 g) was then added, and subsequently the complex $CoCl_2$(L4) [sample GL924] (1.56 ml of a toluene solution at a concentration equal to 2 mg/ml; 1×10$^{-5}$ moles, equal to about 3.12 mg) obtained as described in Example 5. The whole was kept, under magnetic stirring, at 20° C., for 45 minutes. The polymerization was then quenched by the addition of 2 ml of methanol containing a few drops of hydrochloric acid. The polymer obtained was then coagulated by the addition of 40 ml of a methanol solution containing 4% of Irganox® 1076 antioxidant (Ciba), obtaining 1.4 g of polybutadiene having a content of 1,4-cis units equal to 97.2%: further characteristics of the process and polybutadiene obtained are indicated in Table 1.

Figure 6:
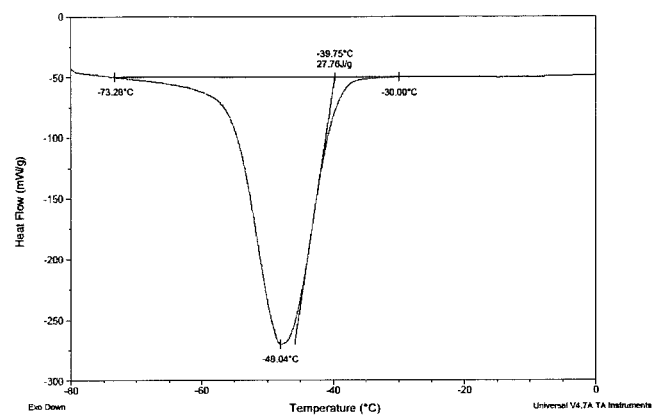
FIG. 6: DSC diagrams of the polybutadiene of Example 10: (A) crystallization; (B) melting.
Figure 6:
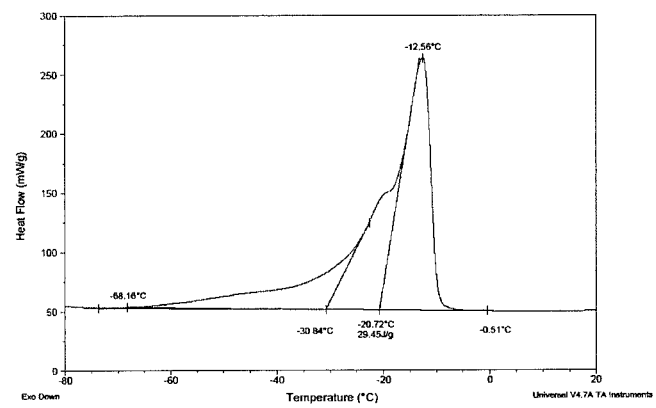

FIG. 6 shows the DSC diagrams of the polybutadiene obtained.

Figure 7:
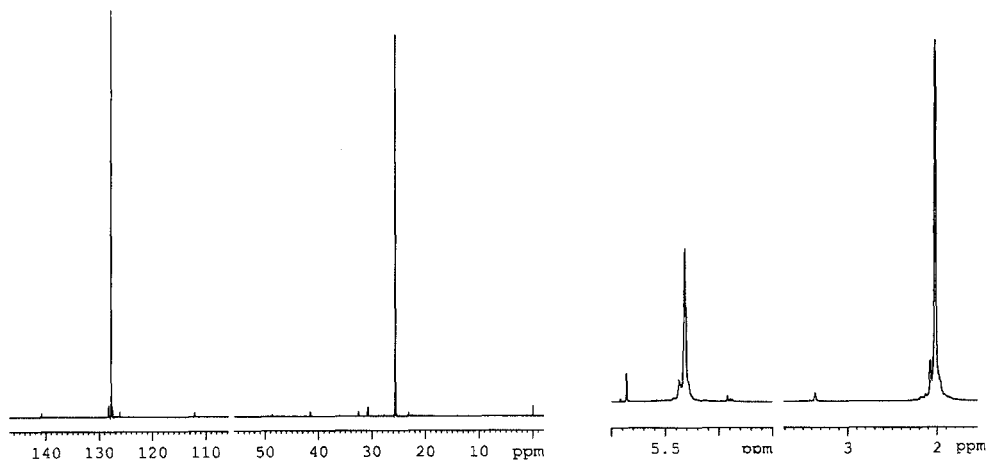
FIG. 7: $^{13}$C-NMR spectrum (on the left) and $^1$H-NMR spectrum (on the right) of the polybutadiene of Example 10.

FIG. 7 shows the $^1$H-NMR and $^{13}$C-NMR spectra of the polybutadiene obtained.

Example 11

GL979

2 ml of 1,3-butadiene equal to about 1.4 g were condensed at a low temperature (−20° C.) in a 25 ml test-tube. 8.1 ml of toluene were then added, and the temperature of the solution thus obtained was brought to 50° C. Methylaluminoxane (MAO) in a toluene solution (6.3 ml; 1×10$^{-2}$ moles, equal to about 0.58 g) was then added, and subsequently the complex $CoCl_2$(L4) [sample GL924] (1.56 ml of a toluene solution at a concentration equal to 2 mg/ml; 1×10$^{-5}$ moles, equal to about 3.12 mg) obtained as described in Example 5. The whole was kept, under magnetic stirring, at 50° C., for 10 minutes. The polymerization was then quenched by the addition of 2 ml of methanol containing a few drops of hydrochloric acid. The polymer obtained was then coagulated by the addition of 40 ml of a methanol solution containing 4% of Irganox® 1076 antioxidant (Ciba), obtaining 1.34 g of polybutadiene having a content of 1,4-cis units equal to 97.2%: further characteristics of the process and polybutadiene obtained are indicated in Table 1.

Figure 8:
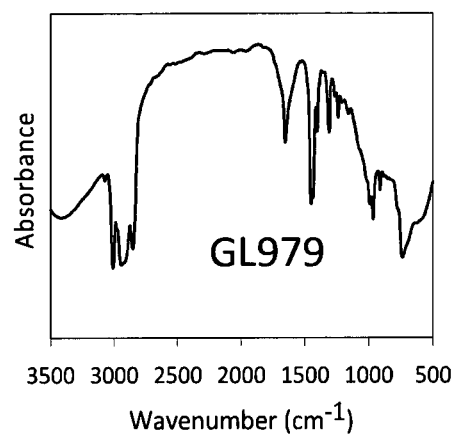
FIG. 8: FT-IR spectrum of the polybutadiene of Example 11 (GL979)

FIG. 8 shows the FT-IR spectrum of the polybutadiene obtained.

Figure 9:
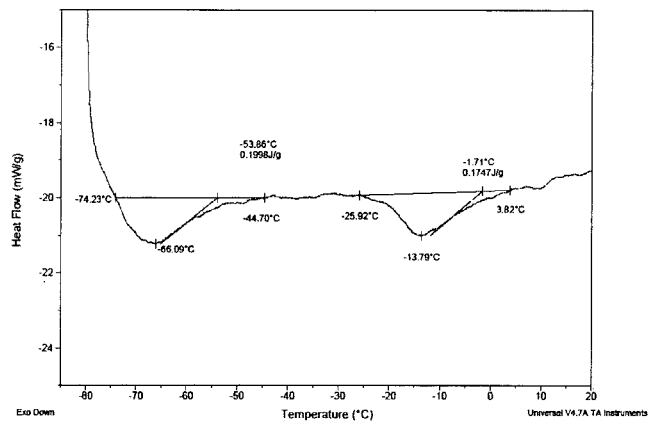
FIG. 9: DSC diagrams of the polybutadiene of Example 11: (A) crystallization; (B) melting.
Figure 9:
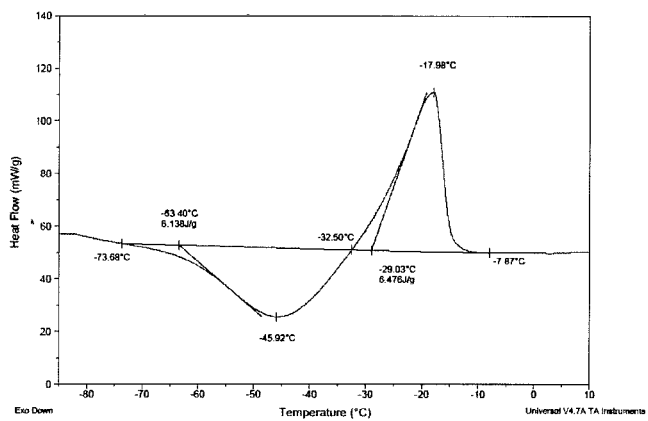

FIG. 9 shows the DSC diagrams of the polybutadiene obtained.

Example 12

GL969

2 ml of 1,3-butadiene equal to about 1.4 g were condensed at a low temperature (−20° C.) in a 25 ml test-tube. 7.9 ml of toluene were then added, and the temperature of the solution thus obtained was brought to 20° C. Methylaluminoxane (MAO) in a toluene solution (6.3 ml; $1\times10^{-2}$ moles, equal to about 0.58 g) was then added, and subsequently the complex $CoCl_2(L6)$ [sample GL927] (1.8 ml of a toluene solution at a concentration equal to 2 mg/ml; $1\times10^{-5}$ moles, equal to about 3.6 mg) obtained as described in Example 6. The whole was kept, under magnetic stirring, at 20° C., for 90 minutes. The polymerization was then quenched by the addition of 2 ml of methanol containing a few drops of hydrochloric acid. The polymer obtained was then coagulated by the addition of 40 ml of a methanol solution containing 4% of Irganox® 1076 antioxidant (Ciba), obtaining 1.4 g of polybutadiene having a content of 1,4-cis units equal to 97.9%: further characteristics of the process and polybutadiene obtained are indicated in Table 1.

Figure 10:
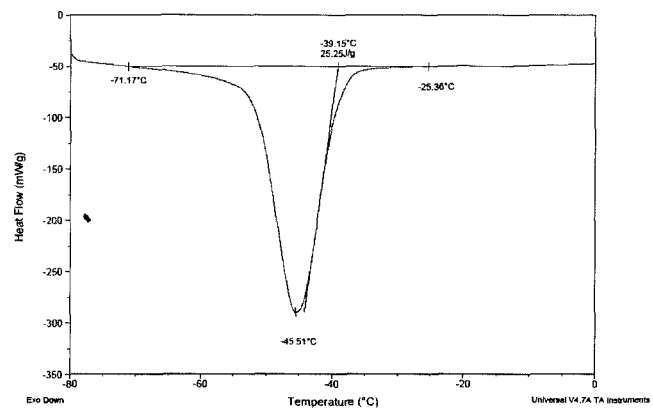
FIG. 10: DSC diagrams of the polybutadiene of Example 12: (A) crystallization; (B) melting.
Figure 10:
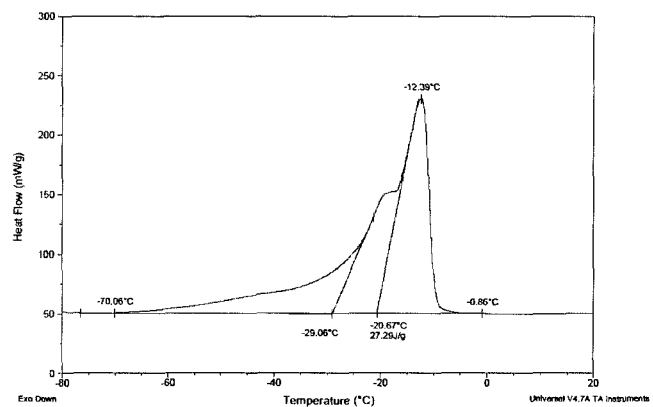

FIG. 10 shows the DSC diagrams of the polybutadiene obtained.

TABLE 1

Polymerization of 1,3-butadiene with catalytic systems comprising complexes of cobalt

| Example | Times (min) | Conversion (%) | $N^{(a)}$ ($h^{-1}$) | $T_m^{(b)}$ (° C.) | $T_c^{(c)}$ (° C.) | $M_w$ (gxmol$^{-1}$) | $M_w/M_n$ | $\alpha^{(e)}$ |
|---|---|---|---|---|---|---|---|---|
| 7 | 35 | 82 | 3644 | −13.7 | −50.2 | 195000 | 2.3 | 0.53 |
| 8 | 10 | 67 | 10422 | −16.2 | −65.2 | 169000 | 2.2 | 0.52 |
| 9 | 10 | 70 | 10889 | −17.5 | −66.6 | 171000 | 2.0 | 0.52 |
| 10 | 45 | 100 | 3457 | −12.6 | −48.0 | 185000 | 2.1 | 0.53 |
| 11 | 10 | 96 | 14933 | −18.0 | −66.1 | 110000 | 2.0 | 0.52 |
| 12 | 90 | 100 | 1728 | −12.4 | −45.5 | 186000 | 2.3 | 0.51 |

$^{(a)}$number of moles of 1,3-butadiene polymerized per hour, per mole of cobalt;
$^{(b)}$melting point;
$^{(c)}$crystallization temperature;
$^{(e)}$linearity index of polybutadiene.

The invention claimed is:

1. An oxo-nitrogenated complex of cobalt having general formula (I):

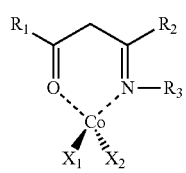

wherein:
R$_1$ and R$_2$, the same or different, represent a hydrogen atom, or they are selected from linear or branched $C_1$-$C_{20}$ alkyl groups optionally halogenated, cycloalkyl groups optionally substituted; or aryl groups optionally substituted;

R$_3$ represents a hydrogen atom, or it is selected from linear or branched $C_1$-$C_{20}$ alkyl groups optionally halogenated, or cycloalkyl groups optionally substituted; or aryl groups optionally substituted; or R$_3$ represents a ketoimine group having formula:

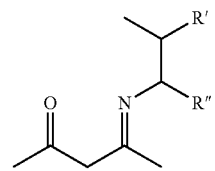

wherein R' and R'', the same or different, represent a hydrogen atom, or they are selected from linear or branched $C_1$-$C_{20}$ alkyl groups, cycloalkyl groups optionally substituted; aryl groups optionally substituted;

X$_1$ and X$_2$, the same or different, represent a halogen atom; or they are selected from linear or branched $C_1$-$C_{20}$ alkyl groups, —OCOR$_4$ groups or —OR$_4$ groups wherein R$_4$ is selected from linear or branched $C_1$-$C_{20}$ alkyl groups.

2. The oxo-nitrogenated complex of cobalt having general formula (I) according to claim 1, wherein:
R$_1$ and R$_2$, the same as each other, represent a hydrogen atom, or they are selected from linear or branched $C_1$-$C_{20}$ alkyl groups;

R$_3$ is selected from linear or branched $C_1$-$C_{20}$ alkyl groups, or phenyl groups optionally substituted with linear or branched $C_1$-$C_{20}$ alkyl groups; or R$_3$ represents a ketoimine group having formula:

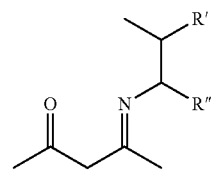

wherein R' and R'', the same as each other, represent a hydrogen atom;
X$_1$ and X$_2$, the same as each other, represent a halogen atom.

3. A catalytic system for the (co)polymerization of conjugated dienes comprising:
(a) at least one oxo-nitrogenated complex of cobalt having general formula (I) according to claim 1;
(b) at least one co-catalyst selected from organic compounds of an element M' different from carbon, said element M' being selected from elements belonging to groups 2, 12, 13 or 14, of the Periodic Table of Elements.

4. The catalytic system for the (co)polymerization of conjugated dienes according to claim 3, wherein said co-catalyst (b) is selected from ($b_1$) aluminium alkyls having general formula (II):

$$Al(X')_n(R_5)_{3-n} \qquad (II)$$

wherein X' represents a halogen atom; R$_5$ is selected from linear or branched $C_1$-$C_{20}$ alkyl groups, cycloalkyl groups, or aryl groups, said groups being optionally substituted with one or more silicon or germanium atoms; and n is an integer ranging from 0 to 2.

5. The catalytic system for the (co)polymerization of conjugated dienes according to claim 3, wherein said co-catalyst (b) is selected from ($b_2$) organo-oxygenated compounds of an element M' different from carbon belonging to groups 13 or 14 of the Periodic Table of Elements.

6. The catalytic system for the (co)polymerization of conjugated dienes according to claim 3, wherein said co-catalyst (b) is selected from ($b_3$) organometallic compounds or mixtures of organometallic compounds of an element M' different from carbon capable of reacting with the oxo-nitrogenated complex of cobalt having general formula (I), extracting therefrom a substituent $X_1$ or $X_2$ σ-bound, to form at least one neutral compound, and an ionic compound including a cation containing the metal (Co) coordinated by the ligand, and a non-coordinating organic anion containing the metal M', wherein the negative charge is delocalized on a multicentric structure.

7. The catalytic system for the (co)polymerization of conjugated dienes according to claim 4, wherein said aluminium alkyls ($b_1$) having general formula (II) are di-ethyl-aluminium chloride (DEAC), mono-ethyl-aluminium dichloride (EADC), ethylaluminiumsesquichloride (EASC).

8. The catalytic system for the (co)polymerization of conjugated dienes according to claim 5, wherein said organo-oxygenated compounds ($b_2$) are selected from aluminoxanes having general formula (III):

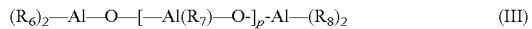

$$(R_6)_2-Al-O-[-Al(R_7)-O-]_p-Al-(R_8)_2 \qquad (III)$$

wherein $R_6$, $R_7$ and $R_8$, the same or different, represent a hydrogen atom, a halogen atom; or they are selected from linear or branched $C_1$-$C_{20}$ alkyl groups, cycloalkyl groups, or aryl groups, said groups being optionally substituted with one or more silicon or germanium atoms; and p is an integer ranging from 0 to 1,000.

9. The catalytic system for the (co)polymerization of conjugated dienes according to claim 8, wherein said organo-oxygenated compound ($b_2$) is methylaluminoxane (MAO).

10. The catalytic system for the (co)polymerization of conjugated dienes according to claim 6, wherein said compounds or mixtures of compounds ($b_3$) are selected from organic compounds of aluminium and boron represented by the following general formulae:

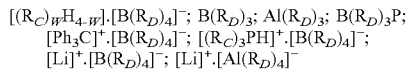

$[(R_C)_wH_{4-w}].[B(R_D)_4]^-$; $B(R_D)_3$; $Al(R_D)_3$; $B(R_D)_3P$;
$[Ph_3C]^+.[B(R_D)_4]^-$; $[(R_C)_3PH]^+.[B(R_D)_4]^-$;
$[Li]^+.[B(R_D)_4]^-$; $[Li]^+.[Al(R_D)_4]^-$ wherein w is an integer ranging from 0 to 3, each group $R_C$ independently represents an alkyl group or an aryl group having from 1 to 10 carbon atoms and each group $R_D$ independently represents an aryl group partially or totally fluorinated, having from 6 to 20 carbon atoms, P represents a pyrrole radical optionally substituted.

11. A process for the (co)polymerization of conjugated dienes, comprising subjecting conjugated dienes to said catalytic system according to claim 1 and forming a (co) polymer of said conjugated dienes.

12. The (co)polymerization process according to claim 11, wherein said conjugated dienes are 1,3-butadiene or isoprene.

13. A polymerization process comprising subjecting 1,3-butadiene or isoprene to said catalytic system according to claim 4 and forming a polymer of 1,3-butadiene or isoprene.

* * * * *